(12) United States Patent
Nakagata et al.

(10) Patent No.: US 9,453,242 B2
(45) Date of Patent: Sep. 27, 2016

(54) METHOD AND CULTURE MEDIUM FOR PREPARING MAMMALIAN OVUM OR EMBRYO IN WHICH ZONA PELLUCIDA HAS BEEN THINNED OR ELIMINATED, AND METHOD FOR FERTILIZATION USING MAMMALIAN OVUM PREPARED BY SAME METHOD

(75) Inventors: Naomi Nakagata, Kumamoto (JP); Toru Takeo, Kumamoto (JP)

(73) Assignee: NATIONAL UNIVERISTY CORPORATION KUMAMOTO UNIVERSITY, Kumamoto (JP)

( * ) Notice: Subject to any disclaimer, the term of this patent is extended or adjusted under 35 U.S.C. 154(b) by 529 days.

(21) Appl. No.: 13/822,171

(22) PCT Filed: Sep. 12, 2011

(86) PCT No.: PCT/JP2011/070687
§ 371 (c)(1),
(2), (4) Date: Jun. 4, 2013

(87) PCT Pub. No.: WO2012/036107
PCT Pub. Date: Mar. 22, 2012

(65) Prior Publication Data
US 2013/0276159 A1 Oct. 17, 2013

(30) Foreign Application Priority Data
Sep. 13, 2010 (JP) .................. 2010-203979

(51) Int. Cl.
| | |
|---|---|
| *C12N 5/075* | (2010.01) |
| *C12N 5/076* | (2010.01) |
| *C12N 5/02* | (2006.01) |
| *C07C 321/00* | (2006.01) |
| *C12N 15/877* | (2010.01) |
| *A01K 67/027* | (2006.01) |
| *C12N 5/073* | (2010.01) |

(52) U.S. Cl.
CPC ......... *C12N 15/8775* (2013.01); *A01K 67/027* (2013.01); *C12N 5/061* (2013.01); *C12N 5/0604* (2013.01); *C12N 5/0609* (2013.01); *A01K 2227/105* (2013.01); *C12N 2500/44* (2013.01); *C12N 2517/10* (2013.01)

(58) Field of Classification Search
CPC C12N 5/0609; C12N 5/061; C12N 2500/44; C12N 5/0604
USPC ................. 435/373, 347, 2, 449; 568/61
See application file for complete search history.

(56) References Cited

FOREIGN PATENT DOCUMENTS

| | | |
|---|---|---|
| JP | 11-346596 | * 12/1999 |
| JP | 2001-061470 | 3/2001 |
| JP | 2004-147604 | 5/2004 |
| JP | 2006-204180 | 10/2006 |
| WO | WO 00/32140 | 6/2000 |

OTHER PUBLICATIONS

Hoshi et al. (1988) Fukushima J. Med. Sci., vol. 34(1), 1-9.*
Bath et al. (Feb. 2010) PLoS One, vol. 5(2), e9387, pp. 1-8.*
Takeo et al. (2008) Biology of Reproduction, vol. 78, 546-551.*
Fan, Zhi Qiang, et al., "Positive effect of partial zona pellucida digestion on in vitro fertilization of mouse oocytes with cryopreserved spermatozoa," Laboratory Animals, vol. 43, pp. 72-77 (2009).
Bath, M.L. "Simple and efficient in vitro fertilization with cryopreserved C57BL/6J mouse sperm." Biol. Reprod., 68:19-23 (2003).
Nakagata, N. et al. "Positive effect of partial zona-pellucida dissection on the in vitro transgenic . . . " Biol. Reprod., 57:1050-1055 (1997).
Kawase, Y. et al. "Effect of partial incision of the zona pellucida by piezo-micromanipulator for in vitro . . . " Biol. Reprod., 66:381-385 (2002).
Kimura, Y. et al. "Intracytoplasmic sperm injection in the mouse" Biol. Reprod., 52:709-720 (1995).
Fong et al. "Ongoing normal pregnancy after transfer of zona-free blastocysts: implications for embryo transfer in the human" Hum Reprod., 12(3):557-560 (1997).
Mary L. Bath "Inhibition of in Vitro Fertilizing Capacity of Cryopreserved Mouse Sperm by Factors Released by Damaged Sperm, and . . . ." PLOS ONE, vol. 5, Issue 2, e9387 (2010).
K. Hoshi, et al. "Effects of agents used for zona pellucida removal on hamster oocyte penetration by hyman spermatozoa" Fukushima J Med Sci. Jun, vol. 34(1), pp. 1-9 (1988).
Takeo, T et al., Methyl-beta-cyclodextrin improves fertilizing ability of C57BL/6 mouse sperm afteer freezing and thawing by . . Biol Reprod. Mar, vol.78 (3), pp. 546-551 2008.
Suzuki, H et al., "Production of a germ-line chimera by coculture of zona-free embryos . . . " J reprod Dev. vol. 40 (4) , pp. 361-365 (1994).

(Continued)

*Primary Examiner* — Anne Marie S Wehbe
(74) *Attorney, Agent, or Firm* — Michael Ye; Andrews Kurth LLP

(57) ABSTRACT

Provided are a method for preparing a mammalian ovum or embryo in which zona pellucida has been thinned or eliminated, and a method for fertilization using the mammalian ovum prepared by the aforementioned method. The method for thinning or eliminating zona pellucida of a mammalian ovum or embryo involves treating or culturing the mammalian ovum or embryo (such as an unfertilized ovum, a fertilized ovum, or an embryo in the early stages of development) in a culture medium containing a reducing agent having SH groups (such as reduced glutathione or DTT). The resulting mammalian ovum or embryo (such as an unfertilized ovum, a fertilized ovum, or an embryo in the early stages of development) in which zona pellucida has been thinned or eliminated is capable of realizing an improved fertilization rate and development rate when used for in vitro fertilization, transplantation of a fertilized ovum, or preparation of an embryo in the early stages of development used in the production of a genetically modified animal.

6 Claims, 11 Drawing Sheets

(56) References Cited

OTHER PUBLICATIONS

International preliminary report on patentability of PCT/JP2011/070687 and Reply to the International preliminary Report on patentability submitted on Feb. 17, 2012.

Hoshi et al. "Effects of agents used for removal of zona pellucida on human sperm penetration into zona-free hamster egg" Acta Obst et Gynaec JPN, vol. 34(12), pp. 2229-2234 1982.

* cited by examiner 0 mM 1 mM 2 mM 10 mM 4 a 4 b 4 c

5a

5b

5c

METHOD AND CULTURE MEDIUM FOR PREPARING MAMMALIAN OVUM OR EMBRYO IN WHICH ZONA PELLUCIDA HAS BEEN THINNED OR ELIMINATED, AND METHOD FOR FERTILIZATION USING MAMMALIAN OVUM PREPARED BY SAME METHOD

CROSS-REFERENCE TO RELATED APPLICATION(S)

The present application relates to and claims priority from International Patent Application No. PCT/JP2011/070687 filed Sep. 12, 2011, which claims the benefit of Japanese Application No. 2010-203979 filed on Sep. 13, 2010. The entire disclosures of the above-identified applications are hereby incorporated by reference in their entireties.

TECHNICAL FIELD

The present invention relates to a technology which can be used for in vitro fertilization and the production of a genetically modified animal. Particularly, the present invention relates to a method for treating an unfertilized ovum, a fertilized ovum or an embryo in the early stages of development of mammals, and to a culture medium which can be used for this method.

BACKGROUND ART

Optical coherence tomography (OCT) provides depth-resolved imaging of biological scattering medium. It has been developed in both time domain and Fourier domain. The conventional time domain system is described in detail by D. Huang et al. [1]. The Fourier domain OCT can be implemented in two ways, which are spectrometer based (called spectral domain OCT, described in U.S. patent application Ser. No. 10/501,276) and swept source based (called optical frequency domain imaging, described in U.S. patent application Ser. No. 10/577,562).

BACKGROUND ART

In fertilization, when a sperm approaching an ovum comes into contact with the zona pellucida of the ovum, an acrosome reaction occurs and acsorome at the anterior part of the head changes to release lytic enzymes such as hyaluronidase, acrosin and the like, and owing to the actions of these enzymes, the sperm passes through zona pellucida and reaches the ovum cell present inside, attaining fertilization. Dysplastic sperms and cryopreserved sperms, however, have lowered fertilizing capacity, and it is difficult to produce a fertilized ovum with these sperms in usual in vitro fertilization in which an ovum and sperms are only mixed. Therefore, there are various developed technologies for enhancing the fertilization rate in in vitro fertilization of mammals.

Now, analysis of gene functions and associated researches and developments are actively conducted worldwide as national projects, and genetically-modified (Tg (Transgenic) and KO (Knock Out)) mice play an important role in them. Since KO mice are produced in sequence, the number of them is believed hereafter to exceed 1000000 kinds, and for keeping their lineages, enormous amount of mice should be bred, and maintenance management of these mice is an extremely serious problem in laboratory animal facilities around the world. So, preservation of these mice by frozen sperms is attracting attention, however, especially sperms of C57BL/6 mice generally used as laboratory animals are often damaged by a freezing treatment and a thawing treatment to lower vital energy and deficient in force for passing through zona pellucida, thus, the fertilization rate thereof is low.

Recently, an improved method for freezing sperms of C57BL/6 mice has been reported (non-patent document 1), however, it is difficult to obtain stable high fertilization rate since this method includes complicated operations, and generally, a fertilization rate of only 10 to 20% is obtained under present circumstances.

Further, a cryopreserved ovum is used in in vitro fertilization when use of a fresh ovum is difficult, however, since zona pellucida hardens by freezing and thawing, there is a problem of lowering of fertilization rate with a freeze-thawed ovum even if fresh sperms are used.

Under such conditions, assisted reproduction technologies as described below are presently used for efficient production of a fertilized ovum in in vitro fertilization using sperms having lowered fertilizing capacity or in in vitro fertilization using a cryopreserved ovum.

For sperms having relatively kept motility, zona pellucida partial dissection methods (PZD: Partial Zona-Pellucida Dissection (non-patent document 2); ZIP: Partial Zona-Pellucida Incision by Piezo-micromanipulator (non-patent document 3)) and a laser zona pellucida drilling method (patent document 1) are used. In the zona pellucida partial dissection method, the zona pellucida of an ovum is cut using a point of a syringe needle (PZD) and a point of a glass capillary tube connected to a Piezo-micromanipulator, and in the laser zona pellucida drilling method, the zona pellucida of an ovum is drilled by laser. Sperms become able to break in an ovum through slits or pores made on zona pellucida, to enhance fertilization rate, by these methods.

In contrast, for sperms showing no motility at all after freezing and thawing, an intracytoplasmic sperm injection method (ICSI: Intra Cytoplasmic Sperm Injection) in which one sperm is mechanically injected directly into ooplasm (non-patent document 4) is used in general.

However, these methods need special technologies and apparatuses and thus cause a problem of low versatility.

Zona pellucida has also a function of protecting a fertilized ovum (fertilized embryo). Zona pellucida is a membrane present around an ovum, and a fertilized ovum is enclosed and protected by zona pellucida and grows under this condition until predetermined time, and then, break away from zona pellucida and nidate.

However, implantation into uterus may be impaired when an embryo in the early stages of development (blastocyst-stage embryo) cannot hatch zona pellucida in the development stage. Such an impairment tends to occur when an ovum having dysplastic zona pellucida is used, when in vitro fertilization is conducted using a cryopreserved ovum or when a fertilized ovum (embryo) is cryopreserved, then, thawed and implanted into uterus, in addition to the case of hardening or thickening of the zona pellucida of an ovum obtained in maturing a follicle using an ovulation inducing drug.

For a fertilized ovum obtained by in vitro fertilization to easily nidate, an assist hatching method (zona drilling) is used before implantation into uterus. The assist hatching method includes a zona pellucida partial dissection method for mechanically cutting zona pellucida using a point of a syringe needle or a glass capillary tube (non-patent documents 2 and 3), a method for drilling zona pellucida by laser (patent document 1) and a method for lysing zona pellucida with an enzyme (non-patent document 5)

However, the method of using a point of a syringe needle or a glass capillary tube and the method for drilling zona pellucida by laser need special apparatuses and technologies and have a problem of low versatility. The method with an enzyme has a problem of lowering of a developmental ability due to damage on an embryo.

Genetically modified animals, for example, genetically-modified mice (knockout mice) are generally produced by the following procedures. First, targeting vectors (recombinant DNA) are prepared, then, the targeting vectors are introduced into ES cells by an electroporation method and the like. ES cell strains which have undergone homologous gene recombination are selected. Next, a chimera is produced by a method in which ES cells are injected by using a micro-manipulator into a cavity formed in a fertilized ovum at the blastocyst stage to produce a chimera embryo, and this chimera embryo is transplanted into the uterus of a pseudo-pregnant mouse (injection chimera production method) and a method in which an embryo in the early stages of development (for example, 8-cell stage embryo) from which zona pellucida has been eliminated is produced, ES cells are added to this and an aggregated lump is made, which is incubated until the blastocyst stage and transplanted into the uterus of a pseudo-pregnant mouse (aggregation chimera method). Then, offsprings (chimera mice) are obtained. Next, the produced chimera mouse and a wild type mouse are mated, and it is confirmed whether the germ cells are formed by cells derived from recombinant ES cells. Then, mice in which formation of the germ cells by cells derived from recombinant ES cells has been confirmed are mutually mated, and knockout mice are selected from the resultant offsprings.

The micro-manipulator method used in the above-described method needs special apparatuses and technologies. By contrast, in the aggregation chimera method, elimination of zona pellucida of an embryo in the early stages of development is necessary, and Acidic Tyrode's solution (pH 2) is used for elimination of zona pellucida (patent document 2). When Acidic Tyrode's solution is used, there is a problem of high cytotoxicity of the Acidic Tyrode's solution itself, and there is a problem that it should be used under protein-free condition during the operation and an embryo in the early stages of development adheres to a dish or a glass capillary to lower operability extremely.

In addition to the above-described assisted reproduction technologies, those related to culture media and culturing methods are suggested such as a method for pre-incubating sperms in a culture medium containing a cyclodextrin derivative and an amino acid and/or a glycolytic intermediate substance for raising fertilization rate (patent document 3), a method in which an unfertilized ovum is added to sperms pre-incubated in a reduced glutathione-containing culture medium and fertilization is performed in the presence of reduced glutathione, to prevent lowering of fertilization rate due to hydrogen peroxide generated in using freeze-thawed sperms (non-patent document 6), and a continuous culturing system and a process for enhancing pregnancy efficiency in human in vitro fertilization (patent document 4), and the like.

PRIOR ART DOCUMENT

Patent Document

Patent document 1: Japanese Unexamined Patent Application Publication No. 2004-147604.

Patent document 2: Japanese Unexamined Patent Application Publication No. 2006-204180.

Patent document 3: Japanese Unexamined Patent Application Publication (Translation of PCT Application) No. 2003-517276.

Patent document 4: Japanese Unexamined Patent Application Publication No. 2001-61470.

Non-Patent Document

Non-patent document 1: Bath, M. L. (2003) Simple and efficient in vitro fertilization with cryopreserved C57BL/6J mouse sperm. Biol. Reprod., 68:19-23.

Non-patent document 2: Nakagata, N., M. Okamoto, O. Ueda, and H. Suzuki (1997) The positive effect of partial zona-pellucida dissection on the in vitro fertilizing capacity of cryopreserved C57BL/6J transgenic mouse spermatozoa of low motility. Biol. Reprod., 57:1050-1055.

Non-patent document 3: Kawase, Y., T. Iwata, O. Ueda, N. Kamada, T. Tachibe, Y. Aoki, K. Jishage, and H. Suzuki (2002) Effect of partial incision of the zona pellucida by piezo-micromanipulator for in vitro fertilization using frozen-thawed mouse spermatozoa on the developmental rate of embryos transferred at the 2-cell stage. Biol. Reprod., 66:381-385.

Non-patent document 4: Kimura, Y. and R. Yanagimachi (1995) Intracytoplasmic sperm injection in the mouse. Biol. Reprod., 52:709-720.

Non-patent document 5: Fong C Y, Bongso A, Ng S C, Anandakumar C, Trounson A, Ratnam S. (1997) Ongoing normal pregnancy after transfer of zona-free blastocysts: implications for embryo transfer in the human. Hum Reprod., 12(3):557-60.

Non-patent document 6: Bath, M. L. (2010) Inhibition of In Vitro Fertilizing Capacity of Cryopreserved Mouse Sperm by Factors Released by Damaged Sperm, and Stimulation by Gultathione., PLOS ONE, Vol. 5, Issue 2, e9387.

SUMMARY OF THE INVENTION

Problem to be Solved by the Invention

In in vitro fertilization, sperms showing low fertilizing capacity such as dysplastic sperms or cryopreserved sperms cannot pass through ovum zona pellucida, and it is difficult to efficiently produce a fertilized ovum in usual in vitro fertilization, thus, thinning or elimination of ovum zona pellucida is necessary in fertilization. Also when a frozen ovum is used, zona pellucida hardens and it is difficult to efficiently produce a fertilized ovum in usual in vitro fertilization, thus, the same treatment is necessary in fertilization.

In in vitro fertilization, implantation into uterus may be impaired since an embryo in the early stages of development (blastocyst embryo) cannot hatch zona pellucida, after production of a fertilized ovum, and in such a case, thinning or elimination of zona pellucida impairing implantation is necessary.

Further, in the production step of a genetically modified animal, it is necessary to produce an embryo in the early stages of development (for example, 2 to 8-cell stage embryo) in which zona pellucida has been eliminated.

The present invention has an object of providing a method in which an improvement in fertilization rate and development rate in a mammalian ovum or embryo can be expected.

Further, the present invention has an object of providing a method for thinning or eliminating the zona pellucida of a mammalian ovum or embryo (for example, an unfertilized ovum, a fertilized ovum or an embryo in the early stages of development), a method for preparing a mammalian ovum and/or embryo (for example, an unfertilized ovum, a fertilized ovum or an embryo in the early stages of development) in which zona pellucida has been thinned or eliminated, and a mammalian ovum or embryo in which zona pellucida has been thinned or eliminated, prepared by the above-described method.

The present invention has another object of providing a method for preparing a mammalian embryo in which zona pellucida has been thinned or eliminated, which can be used for in vitro fertilization, transplantation of a fertilized ovum and preparation of an embryo in the early stages of development utilized in production of a genetically modified animal.

The present invention has a further object of providing the above-described preparation method which at least requires no special technologies and apparatuses, and preferably, of providing a versatile method causing no cytotoxicity or diminishing no experimental operability.

Further, the present invention has another object of providing a culture medium for a mammalian embryo with which the zona pellucida of a mammalian embryo can be thinned or eliminated, which can be used for in vitro fertilization, pretreatment of a fertilized ovum before transplantation, or preparation of an embryo in the early stages of development utilized in production of a genetically modified animal.

Means for Solving the Problem

The present inventors have intensively studied to solved the above-described problems and resultantly found that the zona pellucida of a mammalian ovum or embryo can be thinned or eliminated by treating a mammalian ovum or embryo (an unfertilized ovum, a fertilized ovum or an embryo in the early stages of development) with a reducing agent having SH groups (for example, reduced glutathione and DTT), and that fertilization rate and development rate can be improved by using the mammalian ovum or embryo in which zona pellucida has been thinned or eliminated, leading to completion of the present invention.

The present invention is a method for preparing a mammalian ovum or embryo in which the zona pellucida of the ovum or embryo has been thinned or eliminated by treating a mammalian (human and nonhuman mammal) ovum or embryo with a culture medium containing an effective amount of a reducing agent having SH groups (reduced glutathione, DTT or disulfide reductase).

Further, the present invention is a method for fertilizing a mammalian ovum in which zona pellucida has been thinned or eliminated by treating with a reducing agent having SH groups, with sperms preferably pre-incubated with cyclodextrin.

Another embodiment of the present invention is a method for preparing a mouse embryo in the early stages of development in which zona pellucida has been thinned or eliminated, which can be used for production of a genetically-modified mouse.

A still another embodiment of the present invention is a method for preparing a mammalian fertilized ovum or embryo in which zona pellucida has been thinned or eliminated, which can improve implantation rate.

The present invention is, more specifically, as described below.

(1) A fertilizing method comprising:
  a. a step of pre-incubating mammalian (human or nonhuman mammal) sperms with a culture medium containing 0.1 mM or more and 20 mM or less cyclodextrin and 0.1 mM or more and 10 mM or less calcium,
  b. a step of adding an unfertilized ovum into a medium containing a reducing agent having SH groups at a concentration of 0.25 mM or more and 500 mM or less in terms of SH equivalent, and preparing an unfertilized ovum treated with the reducing agent, for thinning or elimination of the zona pellucida of the unfertilized ovum of a mammal (human or nonhuman mammal), and
  c. a step of conducting fertilization by co-incubating the sperms pre-incubated in the step a with the unfertilized ovum treated with the reducing agent having SH groups in the step b.

(2) The fertilizing method according to (1), wherein the above-described unfertilized ovum is a mouse unfertilized ovum.

(3) The fertilizing method according to (1) or (2), wherein the above-described cyclodextrin is methyl-β-cyclodextrin.

(4) The fertilizing method according to any one of (1) to (3), wherein the step c is a step of adding the sperms pre-incubated in the step a into the culture medium containing the unfertilized ovum treated with the reducing agent having SH groups in the step b and performing insemination.

(5) The fertilizing method according to any one of (1) to (4), wherein the above-described reducing agent having SH groups is reduced glutathione and the concentration of the reduced glutathione in the culture medium is 15 mg/ml or more and 90 mg/ml or less.

(6) The fertilizing method according to any one of (1) to (4), wherein the above-described reducing agent having SH groups is reduced glutathione and the concentration of the reduced glutathione in the culture medium is 0.075 mg/ml or more and 3.0 mg/ml or less.

(7) The fertilizing method according to (6), wherein the concentration of the above-described reduced glutathione in the culture medium is 0.15 mg/ml or more and 0.46 mg/ml or less.

(8) The fertilizing method according to (6) or (7), wherein insemination in the above-described step c is conducted by co-incubating the above-described unfertilized ovum and the above-described sperms for several hours in the same culture medium as in the above-described step b.

(9) The fertilizing method according to (5), wherein insemination in the above-described step c is conducted in a culture medium containing substantially no reduced glutathione.

(10) The fertilizing method according to (1), wherein the sperms used for fertilization are fresh sperms, frozen sperms, refrigerated sperms or a combination thereof, which are pre-incubated in a culture medium containing no reduced glutathione.

(11) The fertilizing method according to (1), wherein the sperms used for fertilization are mouse frozen sperms and pre-incubation of the sperms in the step a is conducted for at least 30 minutes.

(12) A method for preparing a mammalian ovum or embryo in which zona pellucida has been thinned or eliminated, by treating a mammalian (human or nonhuman mammal) ovum or embryo with a medium containing a reducing agent having SH groups (preferably, DTT or reduced glutathione) at a concentration of 0.25 mM or more and 500 mM or less in terms of SH equivalent (in the case of reduced glutathione, a concentration of 0.075 mg/ml or more and 150 mg/ml or less), preferably at a concentration of 0.5 mM or more and 500 mM or less in terms of SH equivalent (in the case of reduced glutathione, a concentration of 0.15 mg/ml or more and 150 mg/ml or less).

(13) The method for preparing a mammalian ovum or embryo in which zona pellucida has been thinned or eliminated according to (12), wherein the above-described mammalian ovum or embryo is a mouse unfertilized ovum or mouse embryo.

(14) The method for preparing a mammalian ovum or embryo in which zona pellucida has been thinned or eliminated according to (12), wherein the above-described mammalian ovum is an unfertilized ovum, and the concentration of the above-described reducing agent having SH groups (preferably, DTT or reduced glutathione) in the culture medium is 0.5 mM or more and 10 mM or less in terms of SH equivalent (in the case of reduced glutathione, a concentration of 0.15 mg/ml or more and 3.0 mg/ml or less), preferably 0.5 mM or more and 1.5 mM or less in terms of SH equivalent (in the case of reduced glutathione, a concentration of 0.15 mg/ml or more and 0.46 mg/ml or less).

(15) The method for preparing a mammalian ovum or embryo in which zona pellucida has been thinned or eliminated according to (12), wherein the concentration of the above-described reducing agent having SH groups (preferably, DTT or reduced glutathione) in the culture medium is 50 mM or more and 500 mM or less in terms of SH equivalent (in the case of reduced glutathione, 15 mg/ml or more and 150 mg/ml or less), preferably 100 mM or more and 300 mM or less in terms of SH equivalent (in the case of reduced glutathione, 30 mg/ml or more and 90 mg/ml or less).

(16) A mammalian ovum or embryo in which zona pellucida has been thinned or eliminated, prepared by the method according to any one of (12) to (15).

(17) A method for preparing a mammalian ovum or embryo in which zona pellucida has been thinned or eliminated, by treating a mammalian (human or nonhuman mammal) ovum or embryo with a medium containing DTT or reduced glutathione at a concentration of 50 mM or more and 300 mM or less in terms of SH equivalent.

(18) The method for preparing a mouse unfertilized ovum and/or a mouse embryo in the early stages of development in which zona pellucida has been thinned or eliminated according to (17), wherein the above-described mammalian ovum or embryo is a mouse unfertilized ovum or a mouse embryo in the early stages of development (2-cell stage embryo to 16-cell stage embryo).

(19) A method for producing a chimera nonhuman mammal, at least comprising a procedure of agglomerating the mouse embryo in the early stages of development prepared by the method according to (18) with an ES cell strain.

(20) A method for enhancing the implantation rate of a mammalian embryo, comprising using the mammalian embryo prepared by the method according to (17).

(21) A mammalian ovum or embryo, prepared by the method according to (17) or (18).

(22) A culture medium for a mammalian ovum or embryo, containing a reducing agent having SH groups (preferably, DTT or reduced glutathione) at a concentration of 0.25 mM or more and 500 mM or less in terms of SH equivalent (in the case of reduced glutathione, a concentration of 0.075 mg/ml or more and 150 mg/ml or less), preferably at a concentration of 0.5 mM or more and 500 mM or less in terms of SH equivalent (in the case of reduced glutathione, a concentration of 0.15 mg/ml or more and 150 mg/ml or less), for thinning or elimination of the zona pellucida of a mammalian (human and nonhuman mammal) ovum or embryo.

(23) A culture medium for incubating an unfertilized ovum for in vitro fertilization or a fertilizing culture medium, containing a reducing agent having SH groups (preferably, DTT or reduced glutathione) at a concentration of 0.25 mM or more and 10 mM or less in terms of SH equivalent (in the case of reduced glutathione, a concentration of 0.075 mg/ml or more and 3.0 mg/ml or less), preferably at a concentration of 0.5 mM or more and 1.5 mM or less in terms of SH equivalent (in the case of reduced glutathione, a concentration of 0.15 mg/ml or more and 0.46 mg/ml or less).

(24) A culture medium for thinning or elimination of the zona pellucida of a mammalian (human or nonhuman mammal) ovum or embryo, containing a reducing agent having SH groups (preferably, DTT or reduced glutathione) at a concentration of 50 mM or more and 300 mM or less in terms of SH equivalent (in the case of reduced glutathione, a concentration of 15 mg/ml or more and 90 mg/ml or less).

(25) The culture medium according to (24), wherein the above-described nonhuman mammal embryo is a receptive embryo or an embryo in the early stages of development for production of a genetically modified animal.

(26) The culture medium according to (25), wherein the above-described genetically modified animal is a genetically modified mouse.

(27) A fertilizing culture medium kit comprising the following media (i) and (ii):
  (i) a sperm pre-incubating culture medium containing 0.1 mM or more and 20 mM or less cyclodextrin and 0.1 mM or more and 10 mM or less calcium, for pre-incubation of sperms of a mammal (human or nonhuman mammal), and
  (ii) a fertilizing culture medium containing a reducing agent having SH groups at a concentration of 0.25 mM or more and 10 mM or less in terms of SH equivalent, for conducting fertilization of an ovum and sperms of a mammal (human or nonhuman mammal).

(28) The fertilizing culture medium kit according to (27), wherein the above-described fertilizing culture medium contains reduced glutathione at a concentration of 0.15 mg/ml or more and 3.0 mg/ml or less.

(29) The fertilizing culture medium kit according to 27 or 28, wherein the above-described sperm pre-incubating culture medium contains substantially no reduced glutathione.

(30) The fertilizing culture medium kit according to any one of (27) to (29), wherein the above-described sperm pre-incubating culture medium is a culture medium selected from the group consisting of a TYH culture medium, an HTF culture medium, a KSOM culture medium, a Dulbeccos's PBS culture medium, an M2 culture medium, a PB1 culture medium, a Hanks culture medium, a Hepes-TALP culture medium, a Hoppe&Pitts culture medium, an m-KRB culture medium, an HIS culture medium, a BO culture medium, an mTALP culture medium, an mT culture medium, an MCM culture medium, a CCM culture medium, a K-MCM culture medium, a BWW culture medium, a Whitten culture medium, a BMOC culture medium, a T6 culture medium, an HT6 culture medium, a Bavister-TALP culture medium, an SOF culture medium, a Menezo-B2 culture medium, a Ham's culture medium, a Medium199 culture medium, an MEM culture medium and an mWM culture medium, and the above-described fertilizing culture medium is a culture medium selected from the group consisting of an HTF culture medium, a TYH culture medium, an mR1ECM culture medium, a BO culture medium, a KSOM culture medium, a Dulbeccos's PBS culture medium, an M2 culture medium, a PB1 culture medium, a Hanks culture medium, a Hepes-TALP culture medium, a Hoppe&Pitts culture medium, an m-KRB culture medium, an HIS culture medium, an mTALP culture medium, an mT culture medium, an MCM culture medium, a CCM culture medium, a K-MCM culture medium, a BWW culture medium, a Whitten culture medium, a BMOC culture medium, a T6 culture medium, an HT6 culture medium, a Bavister-TALP culture medium, an SOF culture medium, a Menezo-B2 culture medium, a Ham's culture medium, a Medium199 culture medium, an MEM culture medium and an mWM culture medium.

(31) The fertilizing culture medium kit according to any one of (27) to (30), wherein the above-described nonhuman mammal is a mouse.

(32) Use of a reducing agent having SH groups (reduced disulfide or DTT), for thinning or elimination of the zona pellucida of a mammalian (human or nonhuman mammal) ovum or embryo.

(33) Use of a reducing agent having SH groups (reduced disulfide or DTT) for increasing fertilization rate by thinning or eliminating the zona pellucida of an unfertilized ovum, in fertilization of an unfertilized ovum of a mammal (human or nonhuman mammal) with sperms thereof, preferably of a mouse unfertilized ovum with mouse sperms (fresh sperms, refrigerated sperms or frozen sperms) pre-incubated in a cyclodextrin-containing culture medium.

Effect of the Invention

According to the present invention, dramatic facilitation of an operation and significant increase in working efficiency can be realized in in vitro fertilization of mammals, particularly a mouse, without requiring a special apparatus. Further, the present invention can be utilized as a technology for making implantation easy or as a technology useful for production of genetically modified animals, particularly a genetically modified mouse. Since glutathione itself is an organism-derived component present as a defense factor, glutathione shows extremely low toxicity to an ovum and an embryo and can be safely used.

DESCRIPTION OF EMBODIMENTS

Figure 1:
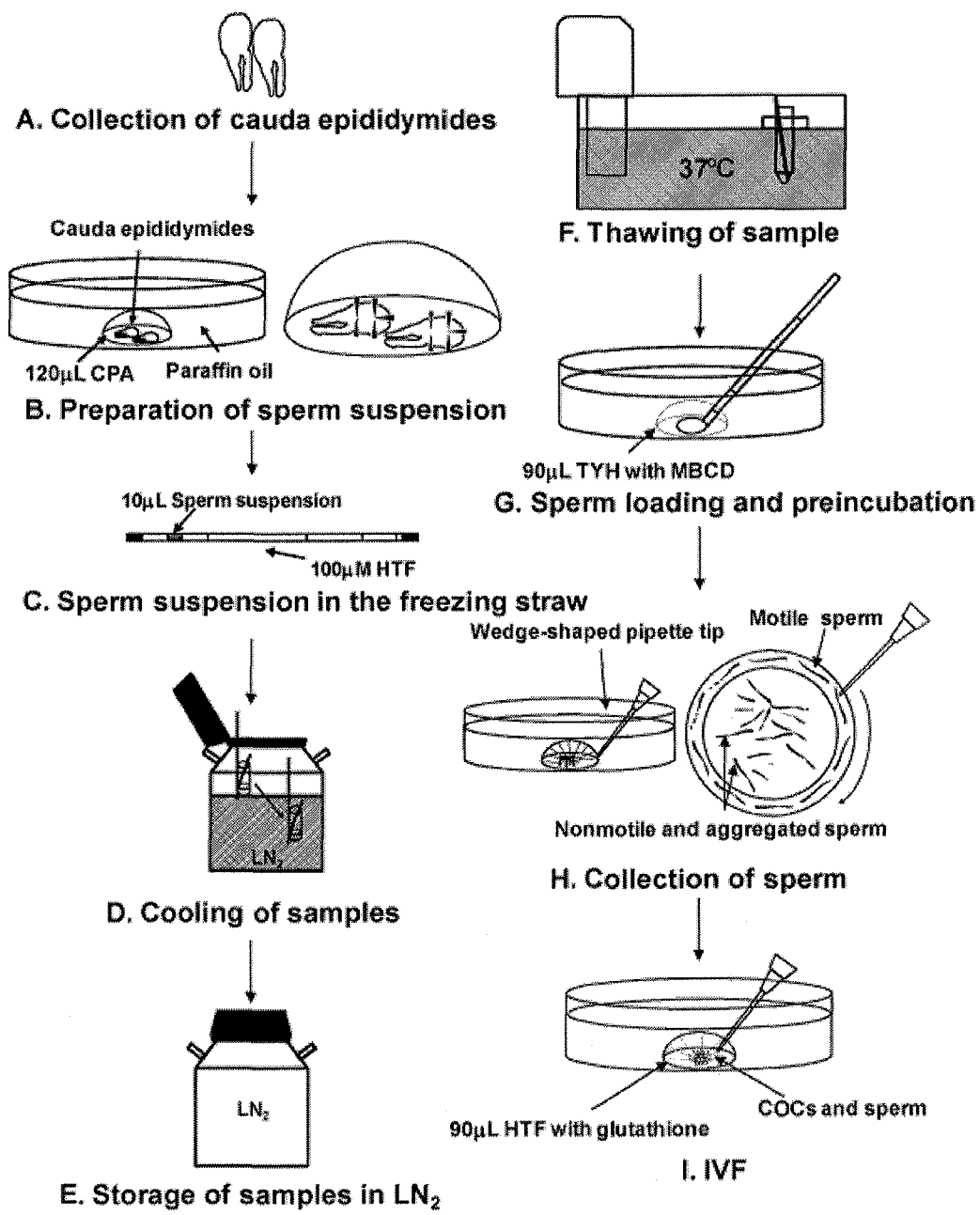
FIG. 1 is a flow chart showing the outline of a method of in vitro fertilization using mouse cryopreserved sperms, used in the present invention.

In the present specification, when the expression "X to Y" is used, X means the lower limit and Y means the upper limit. In the present specification, "glutathione" and "reduced glutathione" are interchangeable terms unless otherwise stated.

The term "thinning of zona pellucida" used in the present invention means that if the structure of the zona pellucida of an ovum receives the action of a reducing agent having SH groups (for example, reduced glutathione or DTT), disulfide bonds in the zona pellucida are cut and the zona pellucida changes or becomes fragile (including also the case accompanied by no apparent change), and according to the circumstances, swelling and other apparent changes occur, and thus sperms become able to pass through the zona pellucida easily under the resultant condition as compare with zona pellucida before receiving the action of glutathione.

The term "containing an effective amount of a reducing agent having SH groups" used in the present invention means that a reducing agent having SH groups (for example, reduced glutathione or DTT) is contained in an amount or at a concentration with which the zona pellucida of an ovum can be thinned or eliminated.

Mammals providing the mammalian ovum and/or embryo (unfertilized ovum, fertilized ovum and/or embryo in the early stages of development) used in the present invention are not particularly restricted, and include all animal species such as, for example, human, livestock animal such as pig, cow, goat, sheep, rabbit and the like, laboratory animals such as mouse, rat, hamster, guinea pig, monkey and the like, pets such as cat, dog and the like, wild animals and the like, and preferable are laboratory animals such as mouse, rat, hamster and the like, and mouse is particularly preferable. As the mouse, any of naturally generated mice and genetically modified mice can be used, and examples thereof include lineages such as BALB/c, CH3/He, C57BL/6J, C57B/6N, DBA/2N, ICR, BDF1, B6C3F1, 129T2/SvEmsJ and the like. Of them, BALB/c and 129 lineages are preferable as the subject matter of the present invention.

The term "mammalian embryo" used in the present invention includes unfertilized ovums, fertilized ovums and embryos in the early stages of development (from 2-cell stage to blastocyst stage) derived from mammals, and means to include all of them unless otherwise stated. The term "mammalian ovum" used in the present invention includes unfertilized ovums and fertilized ovums derived from mammals, and means to include both ovums unless otherwise stated. The term "mammalian embryo" used in the present invention means an embryo in the early stages of development, for example, a 2-cell stage to blastocyst stage embryo.

As the mammalian ovum and/or embryo (unfertilized ovum, fertilized ovum and/or embryo in the early stages of development) used in the present invention, those collected from mammals may be directly used, or these may be refrigerated or cryopreserved, then, thawed and used. Refrigeration, cryopreservation and thawing can be conducted according to ordinary methods in the technological field of in vitro fertilization.

The term "unfertilized ovum" used in the present invention includes ovums (embryos) in fresh condition after collecting from an individual, ovums refrigerated until use after collection, and ovums which are cryopreserved, then, thawed and used, and means to include all of them unless otherwise stated.

The term "fertilized ovum" used in the present invention includes ovums (embryos) after fertilization and fertilized ovums (embryos) thawed after freezing, and means to include both ovums unless otherwise stated.

The "embryo in the early stages of development" used in the present invention includes 2-cell stage to blastocyst stage embryos. Further, the term "embryo in the early stages of development" includes embryos in the early stages of development and these embryos thawed after freezing, and means to include both embryos unless otherwise stated.

The reducing agent having SH groups used in the present invention includes reduced glutathione, DTT and disulfide reductases (for example, glutathione reductase and thioredoxin), and preferable is reduced glutathione or DTT, and reduced glutathione is particularly preferable.

As the reduced glutathione to be used in the present invention, commercially available reduced glutathione can be used as it is, and commercially available oxidized glutathione may be reduced before use.

The concentration of the reducing agent having SH groups used in the present invention is, in the case of reduced glutathione or DTT, 0.25 mM or more and 500 mM or less, more preferably 0.5 mM or more and 300 mM or less, particularly preferably 1.0 mM or more and 200 mM or less in terms of SH equivalent, and can be appropriately selected depending on its object, and a preferable concentration depending on its object is present.

When reduced glutathione is used as the reducing agent having SH groups in the present invention, the concentration of reduced glutathione in the culture medium is preferably 0.075 mg/ml or more and 150 mg/ml or less, more preferably 0.15 mg/ml or more and 90 mg/ml or less, particularly preferably 0.30 mg/ml or more and 60 mg/ml or less, and the concentration can be appropriately selected depending on its object, and a preferable concentration depending on its object is present.

When DTT is used as the reducing agent having SH groups in the present invention, the concentration of DTT in the culture medium is preferably 0.125 mM or more and 250 mM or less, more preferably 0.25 mM or more and 150 mM or less, particularly preferably 0.5 mM or more and 100 mM, and the concentration can be appropriately selected depending on its object, and a preferable concentration depending on its object is present.

When the disulfide reductase is used as the reducing agent having SH groups in the present invention, the enzyme is added in the culture medium at a concentration of 0.01 mg/ml or more and 100 mg/ml or less, preferably 0.1 mg/ml or more and 10 mg/ml or less and the reaction thereof is carried out at 20 to 37° C. for 0.5 to 24 hours, preferably 1 to 8 hours, and the concentration and the reaction time can be appropriately selected depending on its object, and preferable conditions depending on its object are present.

The concentration of reduced glutathione having SH groups in the culture medium in the present invention when intending thinning of the zona pellucida of a mammalian ovum or embryo and the concentration thereof when intending elimination of zona pellucida can be different. For example, when reduced glutathione is used as the reducing agent having SH groups, the concentrations as shown below can be used.

When intending thinning of the zona pellucida of a mammalian ovum or embryo, the concentration of glutathione used in the present invention is preferably 0.075 mg/ml or more and 15 mg/ml or less, more preferably 0.15 mg/ml or more and 3.0 mg/ml or less, further preferably 0.15 mg/ml or more and less than 0.46 mg/ml, particularly preferably 0.30 mg/ml or more and less than 0.46 mg/ml in the culture medium. A sufficient effect can be manifested for thinning of zona pellucida, even if the concentration of glutathione in the culture medium is a lower concentration in the above-described range, for example, within a range of 0.15 mg/ml or more and less than 0.46 mg/ml.

When intending thinning of zona pellucida, a sufficient effect can be manifested at a lower concentration of glutathione used in the present invention, in the case of treating or incubating a mammalian ovum or embryo for relatively longer time, for example, dozens of minutes to several hours. The concentration of glutathione in this case is preferably 0.075 mg/ml or more and 6.0 mg/ml or less, more preferably 0.15 mg/ml or more and 3.0 mg/ml or less, further preferably 0.15 mg/ml or more and less than 0.46 mg/ml, particularly preferably 0.30 mg/ml or more and less than 0.46 mg/ml. By treating or incubating an unfertilized ovum at these concentrations, fertilization rate improves by 20% to 60%, and even if whichever of frozen sperms, refrigerated sperms and fresh sperms is used, its fertilization rate rises significantly.

When intending thinning of zona pellucida, a sufficient effect can be manifested at a middle concentration of glutathione used in the present invention, in the case of treating or incubating a mammalian ovum or embryo for relatively shorter time, for example, dozens of seconds to several minutes. The concentration of glutathione in this case is preferably 6.0 mg/ml or more and less than 15 mg/ml, more preferably 6.0 mg/ml or more and 12 mg/ml or less. Fertilization rate improves by incubating an unfertilized ovum at these concentrations for relatively shorter time, then, removing glutathione from the culture medium, and fertilizing the ovum with sperms. Treating at a middle concentration is particularly effective in the case of an unfertilized ovum (for example, freeze-thawed ovum) or species (for example, large animals such as livestock animals and the like) revealing an insufficient effect by treatment at a lower concentration.

When intending elimination of the zona pellucida of a mammalian ovum or embryo, the concentration of glutathione used in the present invention is preferably 15 mg/ml or more and 150 mg/ml or less, more preferably 15 mg/ml or more and 90 mg/ml or less, further preferably 30 mg/ml or more and 90 mg/ml or less, particularly preferably 30 mg/ml or more and 60 mg/ml or less in the culture medium. Zona pellucida can be easily removed if an unfertilized ovum, a fertilized ovum or an embryo in the early stages of development (for example, 8-cell stage embryo) is treated at these concentration for shorter time (for example, 10 seconds to several minutes, preferably 30 seconds to 120 seconds).

The above-described range of the glutathione concentration is a particularly preferable range for a mouse unfertilized ovum, fertilized ovum or embryo in the early stages of development, and the concentration of glutathione can be appropriately selected depending on the condition of an intended unfertilized ovum, fertilized ovum or embryo in the early stages of development (fresh embryo, refrigerated embryo or freeze-thawed embryo) and the kind thereof, within the above-described range. The preferable range of the glutathione concentration can be appropriately selected depending on the size of an unfertilized ovum, a fertilized ovum or an embryo in the early stages of development varying depending on the difference of mammalian species, and when a larger embryo (for example, cow embryo) as compared with a mouse embryo is used, it is adequate to use glutathione at higher concentration as compared with a mouse embryo. The treating time is appropriately selected, and can be shorter or longer.

Examples using reduced glutathione as the reducing agent having SH groups according to the present invention have been described above, however, in the case of use of DTT, the zona pellucida of a mammalian ovum or embryo can be thinned or eliminated by using DTT of the equal concentration reduced by SH equivalent.

Examples of reduced glutathione will be mainly used to explain the present invention further in detail below, but the present invention is not limited to them.

An unfertilized ovum in which zona pellucida has thus been thinned or eliminated is useful since in vitro fertilization of this ovum even with sperms showing extremely lower motility is possible. In in vitro fertilization using a freeze-thawed ovum, the zona pellucida of the ovum hardens by freezing and thawing and sperms become unable to penetrate easily, therefore, it is effective to thin or eliminate the zona pellucida using the present invention. Further, in production of a genetically modified animal, the zona pellucida of an embryo in the early stages of development (for example, 2-cell to 8-cell stage embryo) can be removed using the present invention and used for fusion with ES cells.

The above-described concentration for thinning or elimination of the zona pellucida of a mammalian ovum or embryo is only rough indication for thinning of zona pellucida or for eliminating zona pellucida, and a case of removal of zona pellucida when the concentration is in the range for thinning of zona pellucida is not excluded and a case of thinning of zona pellucida when the concentration is in the rage for removal of zona pellucida is not excluded.

When the method of the present invention is used for in vitro fertilization, an unfertilized ovum may be treated with a glutathione or DTT-containing culture medium before fertilization, or may be treated with glutathione or DTT-containing culture medium simultaneously with fertilization, in the present invention. It the case of treating with a glutathione-containing culture medium before fertilization, an unfertilized ovum is treated with a glutathione-containing culture medium, for example, a glutathione-containing HTF culture medium for, for example, dozens of seconds to several minutes, or dozens of minutes, then, if necessary, glutathione is removed from the culture medium, and the ovum is used for fertilization. Preferably, an unfertilized ovum is prepared in a glutathione-containing culture medium and treated with glutathione, and if necessary, the culture medium is exchanged for a culture medium containing no glutathione, then, the prepared sperms are added to this and fertilization thereof is conducted. In contrast, in the case of treating an unfertilized ovum with a glutathione-containing culture medium simultaneously with fertilization, a unfertilized ovum is prepared in a glutathione-containing culture medium, and sperms separately prepared are added to this (insemination) and fertilization thereof is conducted. It is preferable that, for example, after treating an unfertilized ovum with a glutathione-containing culture medium, or after initiating the treatment, sperms are added to this, as described above. By this procedure, a lot of unfertilized ovums can be fertilized simultaneously by a simple method.

When an unfertilized ovum is treated with a glutathione-containing culture medium having high glutathione concentration, for example, a concentration of 15 mg/ml or more, for eliminating zona pellucida, it is necessary that glutathione is removed before fertilization.

In the method of the present invention, sperms to be used for fertilization with an unfertilized ovum in which zona pellucida has been thinned or eliminated by the method of the present invention are preferably pre-incubated before use. In such a case, an improvement in fertilization rate can be expected by pre-incubating sperms with a culture medium containing any one of natural or synthesized α-cyclodextrin, β-cyclodextrin, γ-cyclodextrin or derivatives thereof, or a combination of any two or more of them. Particularly, in the case of use of frozen sperms having lowered fertilizing capacity, a significant improvement in fertilization rate can be expected.

As cyclodextrin, any one of synthesized materials, natural substances or derivatives thereof may be used, and examples of the cyclodextrin derivate include those having an α-cyclodextrin skeleton in which six glucoses are circularly linked via an α-1,4 linkage, those having a β-cyclodextrin skeleton in which seven glucoses are circularly linked via an α-1,4 linkage or those having a γ-cyclodextrin skeleton in which eight glucoses are circularly linked via an α-1,4 linkage. Such cyclodextrin derivatives include methyl-β-cyclodextrin, hydroxypropyl-β-cyclodextrin, glucosyl-3-cyclodextrin, maltosyl-β-cyclodextrin, sulfobutyl-β-cyclodextrin, and α-isomers and γ-isomers thereof, and preferable is methyl-β-cyclodextrin. The concentration of cyclodextrin or its derivative in pre-incubation is appropriately selected depending on the kind of cyclodextrin to be used, and for example, it is preferably 0.1 mM or more and 20 mM or less, more preferably 0.2 mM or more and 10 mM or less, particularly preferably 0.5 mM or more and 5 mM or less, and in the case of methyl-β-cyclodextrin, for example, it is preferably 0.5 mM or more and 5 mM or less, further preferably 0.5 mM or more and 3.0 mM or less.

In pre-incubation of sperms, it is preferable to add calcium to the culture medium for activating fertilizing capacity. The concentration of calcium in the culture medium is, for example, 0.1 mM or more and 10 mM or less, preferably 0.5 mM or more and 5.0 mM or less, further preferably 1.0 mM or more and 2.0 mM or less, and the optimum concentration in the present invention is about 1.7 mM.

Pre-incubation of sperms is conducted in the above-described culture medium containing dextrin and calcium at about 37° C. for 10 minutes to several hours, preferably 30 minutes to 1 hour. The pre-incubation time can be appropriately selected depending on the kind and condition of sperms (fresh sperms, refrigerated sperms or frozen sperms).

The method for fertilization of a mammalian (human and nonhuman mammal) ovum of the present invention comprises the following steps.

a. a step of pre-incubating mammalian (human or nonhuman mammal) sperms with a culture medium containing 0.1 mM or more and 20 mM or less cyclodextrin and 0.1 mM or more and 10 mM or less calcium, b. a step of adding an unfertilized ovum into a medium containing a reducing agent having SH groups at a concentration of 0.25 mM or more and 500 mM or less in terms of SH equivalent, and preparing an unfertilized ovum treated with the reducing agent, for thinning or elimination of the zona pellucida of the unfertilized ovum of a mammal (human or nonhuman mammal), and c. a step of conducting fertilization by co-incubating the sperms pre-incubated in the step a with the unfertilized ovum treated with the reducing agent having SH groups in the step b.

Here, the unfertilized ovum is not particularly restricted, however, a mouse unfertilized ovum is preferable.

In one embodiment, the reducing agent having SH groups is reduced glutathione or DTT, and reduced glutathione is preferable. The concentration of the reducing agent in the culture medium is 0.25 mM or more and 10 mM or less, preferably 0.5 mM or more and 10 mM or less in terms of SH equivalent, and in the case of reduced glutathione, it is 0.075 mg/ml or more and 3.0 mg/ml or less, preferably 0.15 mg/ml or more and 3.0 mg/ml or less, further preferably 0.15 mg/ml or more and 0.46 mg/ml or less. Particularly, in the case of use of fresh sperms, a remarkable improvement in fertilization rate is attained with reduced glutathione of a concentration of 0.075 mg/ml or more.

In the method for fertilization of an unfertilized ovum of a mammal (human and nonhuman mammal) of the present invention, sperms are pre-incubated with a culture medium containing cyclodextrin and calcium as described above. The concentrations of cyclodextrin and calcium to be added to the culture medium are as described above. An improvement in fertilization rate is obtained by addition of cyclodextrin. When frozen sperms are used, it is particularly preferable that the sperms are pre-incubated with cyclodextrin, and particularly in the case of use of mouse frozen sperms, a remarkable improvement in fertilization rate is obtained. By inclusion of calcium, activation of fertilizing capacity can be expected.

The method for fertilization of an unfertilized ovum of a mammal (human and nonhuman mammal) of the present invention further includes an embodiment, wherein the step c is a step of adding the sperms pre-incubated in the presence of cyclodextrin in the step a into the culture medium containing the unfertilized ovum treated with the reducing agent having SH groups in the step b and performing insemination.

A lot of unfertilized ovums can be fertilized simultaneously by a simple method in which after treating unfertilized ovums with glutathione or after initiating the treatment, sperms are added to them.

The method for fertilization of an unfertilized ovum of a mammal (human and nonhuman mammal) of the present invention is further capable of adding the above-described sperms into the above-described culture medium containing unfertilized ovums, then, co-incubating them for dozens of minutes to several hours, and conducting fertilization while performing thinning or elimination of zona pellucida. The time of co-incubation can be appropriately selected depending on the kind and condition of sperms and an ovum to be used, and incubation conditions and the like, and sufficient fertilization can be expected even by co-incubation for dozens of minutes, and fertilization is completed by co-incubation for several hours. In the case of a mouse, sufficient fertilization can be attained by fertilization for dozens of minutes, and fertilization is completed in about 3 hours. By this, progression of thinning of zona pellucida and fertilization can be conducted simultaneously, and the operation can be carried out efficiently.

In another aspect, the method for fertilization of an unfertilized ovum of a mammal (human and nonhuman mammal) of the present invention comprises a step of eliminating the zona pellucida of an embryo by treating an unfertilized ovum with a culture medium containing a reducing agent having SH groups at a concentration of 50 mM or more and 300 mM or less in terms of SH equivalent in the above-described step, a step of removing the reducing agent having SH groups from the culture medium, and a step of conducting insemination of adding sperms into the medium containing the unfertilized ovum.

Here, when the reducing agent having SH groups is reduced glutathione, it is preferable that the concentration of the reduced glutathione in the culture medium is 15 mg/ml or more and 90 mg/ml or less.

Sperms used in the above-described fertilization methods can be fresh sperms, frozen sperms, refrigerated sperms or a combination thereof, and it is simple and convenient to use frozen sperms. Further, sperms not treated with reduced glutathione can be used.

In one aspect, the culture medium of the present invention is a culture medium for a mammalian embryo, containing reduced glutathione or DTT as the reducing agent having SH groups at a concentration of 0.25 mM or more and 300 mM or less in terms of SH equivalent, for thinning or eliminating the zona pellucida of a mammalian (human and nonhuman mammal) ovum or embryo.

The culture medium for thinning zona pellucida of the present invention is a culture medium containing reduced glutathione or DTT as the reducing agent having SH groups at a concentration of 0.5 mM or more and 10 mM or less in terms of SH equivalent.

The culture medium for eliminating zona pellucida of the present invention is a culture medium containing reduced glutathione or DTT as the reducing agent having SH groups at a concentration of 50 mM or more and 300 mM or less in terms of SH equivalent.

The culture medium of the present invention contains reduced glutathione or DTT as the reducing agent having SH groups at a concentration of 50 mM or more and 300 mM or less, preferably 100 mM or more and 300 mM or less in terms of SH equivalent, in the case of treating or incubating a receptive embryo or an embryo in the early stages of development for production of a genetically modified animal.

The culture medium to be used in the present invention is used without particular restriction in its kind providing it is a fertilizing culture medium containing a reducing agent having SH groups (for example, reduced glutathione or DTT) at prescribed concentration in a culture medium used for preparing or fertilizing an unfertilized ovum. Specifically, for example, an HTF culture medium, a TYH culture medium, an mR1ECM culture medium, a BO culture medium, a KSOM culture medium, a Dulbeccos's PBS culture medium, an M2 culture medium, a PB1 culture medium, a Hanks culture medium, a Hepes-TALP culture medium, a Hoppe&Pitts culture medium, an m-KRB culture medium, an HIS culture medium, an mTALP culture medium, an mT culture medium, an MCM culture medium, a CCM culture medium, a K-MCM culture medium, a BWW culture medium, a Whitten culture medium, a BMOC culture medium, a T6 culture medium, an HT6 culture medium, a Bavister-TALP culture medium, an SOF culture medium, a Menezo-B2 culture medium, a Ham's culture medium, a Medium199 culture medium, an MEM culture medium and an mWM culture medium can be used, and for example, culture media prepared by allowing glutathione to be contained at prescribed concentration in an HTF culture medium, a TYH culture medium, an mR1ECM culture medium and a BO culture medium are preferably used, and culture media prepared by allowing a reducing agent having SH groups (for example, reduced glutathione or DTT) to be contained in an HTF culture medium are particularly preferably used. Here, the TYH culture medium is preferably used for a mouse fertilized ovum, the mR1ECM culture medium is preferably used for a rat fertilized ovum and the BO culture medium is preferably used for a fertilized ovum of livestock animals.

The culture medium used for pre-incubation of sperms in the present invention is used without particular restriction in its kind providing it is a culture medium containing cyclodextrin at prescribed concentration. For example, culture media prepared by allowing cyclodextrin (preferably, methyl-β-cyclodextrin) to be obtained at prescribed concentration in TYH or HTF are preferably used. Specific examples thereof include an HTF culture medium, a TYH culture medium, an mR1ECM culture medium, a BO culture medium, a KSOM culture medium, a Dulbeccos's PBS culture medium, an M2 culture medium, a PB1 culture medium, a Hanks culture medium, a Hepes-TALP culture medium, a Hoppe&Pitts culture medium, an m-KRB culture medium, an HIS culture medium, an mTALP culture medium, an mT culture medium, an MCM culture medium, a CCM culture medium, a K-MCM culture medium, a BWW culture medium, a Whitten culture medium, a BMOC culture medium, a T6 culture medium, an HT6 culture medium, a Bavister-TALP culture medium, an SOF culture medium, a Menezo-B2 culture medium, a Ham's culture medium, a Medium 199 culture medium, an MEM culture medium and an mWM culture medium, and a TYH culture medium is particularly preferably used.

In the present invention, the above-described sperm pre-incubating culture medium and the above-described fertilizing culture medium can be used to give a kit. That is, in another embodiment of the present invention, the present invention is a fertilizing culture medium kid comprising the following sperm pre-incubating culture medium and fertilizing culture medium:

(i) a sperm pre-incubating culture medium containing 1.0 mM or more and 10 mM or less calcium and 0.1 mM or more and 20 mM or less cyclodextrin, for pre-incubation of sperms of a mammal (human or nonhuman mammal), and (ii) a fertilizing culture medium containing a reducing agent having SH groups at a concentration of 0.25 mM or more and 10 mM or less in terms of SH equivalent, for conducting fertilization of an ovum and sperms of a mammal (human or nonhuman mammal).

As examples, the compositions of an HTF culture medium, a TYH culture medium, an mRICE culture medium and a BO culture medium are shown below.

TABLE 1

| HTF culture medium | |
|---|---|
| Reagent name | mg/100 mL |
| NaCl | 593.8 |
| KCl | 35.0 |
| $MgSO_4 \cdot 7H_2O$ | 4.9 |
| $KH_2PO_4$ | 5.4 |
| $CaCl_2$ | 57.0 |
| $NaHCO_3$ | 210.0 |
| Glucose | 50.0 |
| Na-lactate (ml) | 0.34 |
| Na-Pyruvate | 3.7 |
| Potassium Penicillin G | 7.5 |
| Streptomycin sulfate | 5.0 |
| BSA (Alubumin, bovine serum, Fraction V, Fatty Acid-Free) | 400 |
| 0.5% phenol red (ml) | 0.04 |

TABLE 2

| TYH culture medium | |
|---|---|
| Reagents | mg/100 mL |
| NaCl | 697.6 |
| KCl | 35.6 |
| $MgSO_4 \cdot 7H_2O$ | 29.3 |
| $KH_2PO_4$ | 16.2 |
| $NaHPO_4$ | 210.6 |
| Na-pyruvate | 5.5 |
| $CaCl_2 \cdot 2H_2O$ | 25.1 |
| Glucose (D+) | 100.0 |
| Potassium Penicillin G | 7.5 |
| Streptomycin sulfate | 5.0 |
| Bovine serum albumin | 400.0 |

TABLE 3

| mR1ECM culture medium | |
|---|---|
| Reagents | |
| NaCl | 110 mM |
| KCl | 3.2 mM |
| $CaCl_2$ | 2.0 mM |
| $MgCl_2$ | 0.5 mM |
| $NaHCO_3$ | 25.0 mM |
| D-Glucose | 4.5 mM |
| Na-pyruvate | 0.5 mM |
| Na-lactate | 10.0 mM |
| PVA (Cold Water Soluble) | — |
| BSA | 4.0 mg/mL |
| L-Glutamine | 0.1 mM |
| MEM-essential amino acid | 2% |
| MEM-nonessential amino acid | 1% |
| Osmolarity | 290 mOsm |

TABLE 4

| BO culture medium | |
|---|---|
| Reagents | mg/100 mL |
| NaCl | 655.0 |
| KCl | 30.0 |
| $NaH_2PO_4 \cdot 2H_2O$ | 13.0 |
| $MgCl_2 \cdot 6H_2O$ | 10.6 |
| $CaCl_2 \cdot 2H_2O$ | 33.0 |
| $NaHCO_3$ | 310.4 |
| Na-pyruvate | 13.8 |
| Penicillin G | 1.3 |

The method for preparing an unfertilized ovum to which the method of the present invention is applied will be illustrated below using mice as an example. The application of the method of the present invention, however, is not limited to mice.

1. Preparation of Ovum 1-1 Collection of Fresh Unfertilized Ovum

In the method for preparing an unfertilized ovum in which zona pellucida has been thinned or eliminated according to the present invention, a pre-treatment conducted in the art can be adopted, in collecting a fresh unfertilized ovum from a mammal, particularly from a mouse. That is, a female mouse which has undergone superovulation by administration of an ovulation inducer is euthanized and its abdominal part is incised. Uterus, oviducts and ovaries are exteriorized, then, only an oviduct is harvested, and a fresh unfertilized ovum wrapped by cumulus cells is taken out from oviduct ampulla. Specifically, superovulation uses an ovulation inducer, for example, utilizes the follicle maturation effect of follicle stimulating hormonal gonadotropin and the ovulation effect of luteinizing hormonal gonadotropin in combination, and more specifically, superovulation can be performed by administering pregnant mare serum gonadotropin (PMSG) of prescribed concentration and human chorionic gonadotropin (hCG) of prescribed concentration to an adult female mouse (8 to 12-week old), for example, at an interval of 48 hours intraperitoneally (7.5 unit/individual). An unfertilized ovum lump (cumulus-oocyte complex: COC) is harvested from the oviduct ampulla of the superovulated female mouse.

1-2) Removal of Cumulus Cell

The fresh unfertilized ovum lump obtained in the above-described step is subjected to a hyaluronidase treatment, and cumulus cells are removed. Specifically, the fresh unfertilized ovum lump is introduced into an in vitro fertilizing culture medium (HTF culture medium) containing hyaluronidase added (0.1%), treated with hyaluronidase, and washed to obtain an ovum from which cumulus cells have been removed.

1-3) Refrigeration of Unfertilized Ovum

In the case of refrigeration of an unfertilized ovum before use, a cumulus cell-adhered ovum obtained as described in 1) or an ovum from which cumulus cells have been removed by further adding the operation of 2) is transferred into an M2 culture medium, and refrigerated (1 to 15° C.) before use. Refrigeration can be continued for 48 hours.

1-4) Cryopreservation of Unfertilized Ovum

A fresh unfertilized ovum can also be cryopreserved before use. Cryopreservation of an unfertilized ovum is conducted by incubating an ovum from which cumulus cells have been removed in an HTF culture medium containing 20% fetal bovine serum for 10 minutes, then, freezing this.

At room temperature, drops (100 µl) of 1M DMSO (dimethyl sulfoxide) are produced on a dish. 1M DMSO is filtrated directly before use using a disposable filter unit (pore size: 0.22 µm). An embryo to be frozen is transferred calmly onto one drop of 1M DMSO. When the embryo sinks to the bottom of the dish, the embryo is equally-divided and transferred onto the remaining drop of 1M DMSO. The embryo is charged into a cryotube together with a 5 µl of a 1M DMSO solution using a 20 µl type autopipetter, and the tube is transferred into a cooling apparatus of 0° C. Five minutes after, 45 µl of a preservation solution (DAP213) previously cooled at 0° C. is allowed to flow down along the wall in the tube and added calmly. Further five minutes after, the tube is mounted on a cane cooled in liquid nitrogen, and immediately immersed in liquid nitrogen and frozen.

2. Preparation of Sperms 2-1) Preparation of Fresh Sperms

A sperm lump is collected from cauda epididymidis harvested from an adult male mouse (8-week or older), and transferred into a sperm incubation solution (TYH culture medium) (200 µl/2 cauda epididymides) in a dish, and pre-incubated in an incubator (37° C., 5% $CO_2$) for 60 minutes, to give fresh sperms used for fertilization.

2-2) Preparation of Refrigerated Sperms

Cauda epididymidis is harvested from an adult male mouse (8-week or older), transferred into a Lifor culture medium (Lifor (registered trademark) ACF Perfusion Media) in a tube, and refrigerated (1 to 15° C.) to give refrigerated sperms used for fertilization.

2-3) Preparation of Frozen Sperms

Cauda epididymidis harvested from an adult male mouse (12-week or older) is transferred into a sperm cryopreservation solution (for example, FERTIUP (registered trademark), Kyudo Co., Ltd.) (120 µl/2 cauda epididymides) in a dish, and 5 to 6 cuts are made on testis. The dish is allowed to stand still for about 3 minutes to render sperms to be suspended in the preservation solution, then, the cauda epididymidis is taken out from the dish. The residual sperm suspension is frozen as described below.

An HTF culture medium is sucked in an amount of 100 µl into a straw. Next, about 10 µl of an air phase is produced, and finally, the above collected sperm suspension is filled in an amount of 10 µl for each operation in a straw, and immersed in liquid nitrogen and cryopreserved to give frozen sperms to be used.

The cryopreserved sperms are taken out from liquid nitrogen, immersed in hot water of 37° C. and warmed for 10 minutes, then, the thawed sperm suspension is transferred onto a 90 µl drop composed of the TYH culture medium.

3. In Vitro Fertilization

A sperm suspension is pre-incubated in 90 µl of a TYH culture medium at 37° C. for 30 minutes, and under a stereomicroscope, sperms showing motility are collected, avoiding nonmotile sperms, and used for fertilization. The pre-incubated sperm suspension (10 µl) is added to 90 µl of an HTF culture medium (±glutathione) into which cumulus-oocyte complexes (COCs) have been previously introduced (insemination), and these are co-incubated in an incubator for 5 to 6 hours (37° C., 5% $CO_2$), thereby performing fertilization. Thereafter, the ovum is washed with drops of new HTF, and the ovum is observed. Those judged to parthenogenetic (only one pronucleus is recognized in ooplasm) are excluded, and on the following day (24 hours after insemination), only 2-cell stage embryos are selected, and fertilization rate is determined according to the following formula.

In vitro fertilization rate (%)=(number of 2-cell stage embryo)/(number of 2-cell stage embryo+number of unfertilized ovum)×100

4. Transplantation of Fertilized Ovum into Oviduct

Usually, a pronucleus stage fertilized ovum or a 2-cell stage embryo are transplanted into oviduct. However, it is also possible to transplant embryos in other stages of development.

As the receptive female, ICR mice are used, and on the day before transplantation, external genitals are observed and those in the proestrus stage are selected and allowed to live together with vasoligated males. On the following day, those showing vaginal plug are used as the receptive female (on day 1 of pseudopregnancy). The skin and abdominal wall of the anesthetized receptive female are incised, and part of ovary, oviduct and uterus is exposed to the outside of the body through the incised portion, and fat adhered to ovary is fixed by a clamp. A 200 µl drop for transplantation is produced at the center of a dish, and embryos to be transplanted (20/individual) are transferred into the drop for transplantation. Next, 10 embryos are sucked together with a small amount of an incubation solution into a transplantation capillary. About ½ to ⅔ of the circumference of oviduct is incised, and the capillary containing embryos is inserted through the incised portion toward ampulla of oviduct and embryos are transplanted. Also into the opposite oviduct, embryos are transplanted by the same operation procedure.

The offspring rate (implanting rate) after embryo transplantation is determined according to the following formula.

Offspring development rate (%)=(number of offspring)/(number of transplanted embryo)×100

5. Production of Chimera Animal

The method for producing a chimera animal by a co-incubation method to which the method of the present invention is applied will be illustrated below using mice as an example. Particularly, the method of the present invention can be used for preparation of a fertilized embryo. The application of the method of the present invention, however, is not limited to mice.

(A) Preparation of ES Cell

A tube containing ES cells is taken out from a liquid nitrogen tank, and thawed in a water bath of 37° C. The thawed ES cells are suspended in about 5 ml of ESM (DMSO 450 ml, serum 100 ml, non-essential amino acid solution 5 ml, β-mercaptoethanol 5 ml and ESGRO (450,000 units, CHEMICON)), and transferred onto a gelatin-coated dish and incubated for 10 minutes. Subsequently, the supernatant on which ES cells are floating is charged into a centrifugal tube and preserved on ice until used in co-incubation.

(B) Preparation of Receptive Embryo

A female mouse superovulated with PMSG and hCG is, after administration of hCG, mated immediately with an adult male. On the following day, the presence or absence of vaginal plug is confirmed. About 40 to 46 hours after administration of hCG, oviducts are harvested from vaginal plug-confirmed mice and perfused, and 2-cell stage embryos are collected. The collected 2-cell stage embryos are incubated in a drop of a KSOM culture medium, and those developed to the 8-cell stage are used as the receptive embryo.

(C) Production of Mouse Embryo

A receptive embryo is introduced into a 10 μl drop of an HTF culture medium containing 100 mM glutathione, and its zona pellucida is dissolved. When disappearance of zona pellucida is confirmed, 1000 μl of an HTF culture medium is immediately added for dilution. The receptive embryo from which zona pellucida has been removed is transferred in three 100 μl KSOM culture media produced and glutathione is removed completely during the transfer.

(D) Production of Chimera Embryo

A drop (15 μl) of a KSOM culture medium is produced on a dish, and dents are made at the bottom of the dish by an aggregation needle, then, coated by liquid paraffin. Embryos in which zona pellucida has been eliminated are introduced into the dents so that one embryo is introduced in one dent, and ES cells are scattered thereon. Until the next day, incubation is conducted in an incubator of 37° C. and 5% $CO_2$, to obtain chimera embryos developed to the blastocyst stage.

(E) Transplantation of Embryo into Uterus

As the receptive female, ICR mice are used, and on the day before transplantation, external genitals are observed and those in the proestrus stage are selected and allowed to live together with vasoligated males. On the next day, vaginal plug is confirmed, and on day 3 of pseudopregnancy, these are used as the receptive female. The skin and abdominal wall of the anesthetized receptive female are incised, and part of ovary, oviduct and uterus is exposed to the outside of the body through the incised portion, and fat adhered to ovary is fixed by a clamp. A 100 μl drop for transplantation is produced at the center of a dish, and embryos to be transplanted (20/individual) are transferred into the drop for transplantation. Next, 10 embryos are sucked together with a small amount of an incubation solution into a transplantation capillary. A site near the oviduct junction of uterus is incised using a syringe needle, and the capillary containing embryos is inserted toward the uterus vaginal portion side from the ovary side and embryos are transplanted. Also into the opposite uterus side, embryos are transplanted by the same operation procedure.

EXAMPLES

The present invention will be illustrated specifically by examples below, but the present invention is not limited to the following examples.

Preparation of Sperm Cryopreservation Solution (CPA Solution)

As the sperm cryopreservation solution, a CPA culture medium was used instead of a TYH culture medium. The CPA culture medium was prepared as described below.

Raffinose 5-hydrate (1,800 mg), 300 mg of skim milk (BD Difco) and 146 mg of L-glutamine were dissolved in 10 ml of distilled water at 60° C., and further, the solution was warmed in a hot bath for 90 minutes at 60° C. The solution was transferred in an amount of 1.0 ml for each operation into a microcentrifuge tube, and centrifugally treated at 10,000×g for 60 minutes. The supernatant (0.7 ml) was collected, and filtrated through a disposable filter having a pore size of 0.22 mm to give a CPA culture medium, which was then preserved at room temperature and used in experiments.

Example 1

Action of Increasing Fertilization Rate by Glutathione

According to the ordinary method as described above, fresh sperms and frozen sperms of C57BL/6J mice and refrigerated sperms (refrigerated for 2 days) of ICR mice were used to prepare sperm suspensions, which were used for conducting in vitro fertilization. Further, according to the ordinary method as described above, mouse fresh unfertilized ovums were prepared and cumulus-oocyte complexes were obtained.

The HTF culture medium was prepared according to the composition table described above. To the prepared HTF culture medium was added reduced glutathione so that its concentration was 1 mM (0.307 mg/ml), to prepare a glutathione-containing culture medium. Specifically, the HTF culture medium was prepared according to the composition table, and the culture medium was enclosed in an amount of 5 ml for each operation into an ample (component A). Further, 30.7 mg of reduced glutathione (available from SIGMA) and 593.8 mg of NaCl were mixed, then, the mixture was dispensed in one-time use amount (glutathione 1.535 mg/mixture 31.225 mg) (component B). Until use, these reagents were refrigerated, and directly before use, the component A and the component B were mixed and used for insemination. As the control, only the component A (THF culture medium containing no glutathione added) was used.

The method of in vitro fertilization using cryopreserved sperms used in the present invention is shown in FIG. 1.

Specifically, into 90 µl of a HTF culture medium (glutathione concentration: 1 mM) containing cumulus-oocyte complexes (COCs) in a dish were added sperm suspensions (collected motile sperms) of fresh sperms, frozen sperms and refrigerated sperms each in an amount of 10 µl, and fertilization was conducted and fertilization rate was determined according to the above-described theory. An HTF culture medium containing no glutathione was used as the control. The results are shown in Table 5.

TABLE 5

| | fertilization rate (%) | |
|---|---|---|
| | control | glutatione added |
| fresh sperms | 54.5 | 82.5 |
| frozen sperms | 67.7 | 92.1 |
| refrigerated sperms | 8.9 | 63.9 |

By treating unfertilized ovums with glutathione, a significant improvement in fertilization rate was observed in all sperms. Particularly, in in vitro fertilization using refrigerated sperms, its improvement was remarkable.

Example 2

Influence by Glutathione Concentration

Fertilization rate was investigated using various reduced glutathione concentrations, in the same manner as in Example 1. As the sperm, frozen sperms of C57BL/6J mice were used, and processed according to FIG. 1. The results are shown in Table 6 below.

TABLE 6

| glutathione concentration (mM) | number of disseminated oocyte | number of 2-cell stage embryo(%) |
|---|---|---|
| 0.00 | 256 | 166(66) |
| 0.25 | 279 | 187(67) |
| 0.50 | 316 | 251(79) |
| 0.75 | 307 | 252(82) |
| 1.00 | 276 | 254(92) |
| 1.25 | 292 | 272(93) |
| 1.50 | 294 | 262(89) |
| 2.00 | 309 | 285(92) |
| 5.00 | 292 | 251(86) |
| 10.00 | 341 | 276(81) |

By this, an improvement in fertilization rate was confirmed at glutathione concentrations of 0.5 mM (0.15 mg/ml) or more. Particularly, a remarkable improvement in fertilization rate was confirmed at concentrations of 1.0 mM or more and 2.0 mM or less (0.30 mg/ml or more and 0.60 mg/ml or less).

Figure 2:
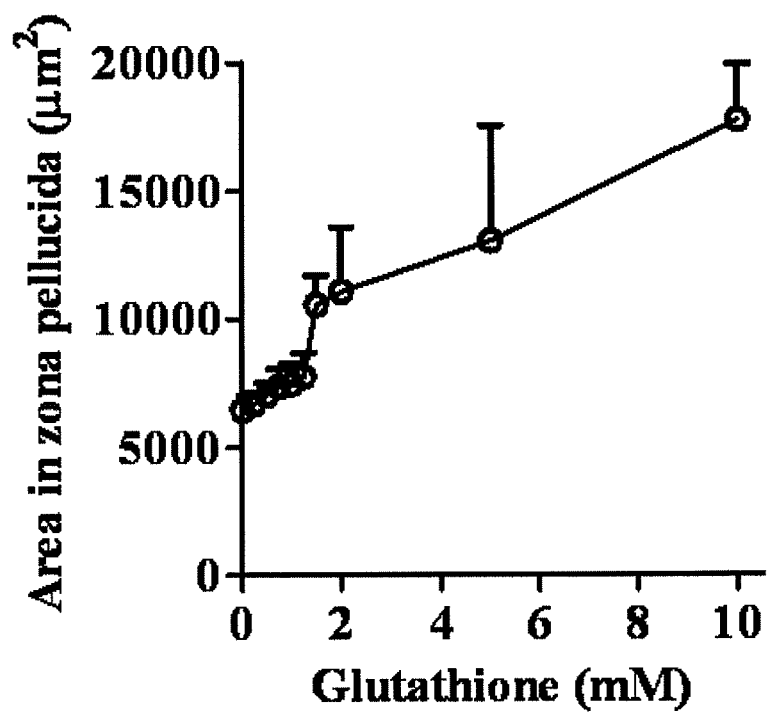
FIG. 2 is a view showing the influence of reduced glutathione on the area in the zona pellucida of a mouse unfertilized ovum.
Figure 3:
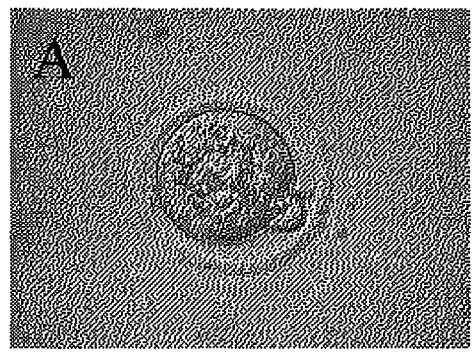
FIG. 3 is a micrograph showing the condition of the zona pellucida of a mouse unfertilized ovum treated with reduced glutathione of each concentration.
Figure 3:
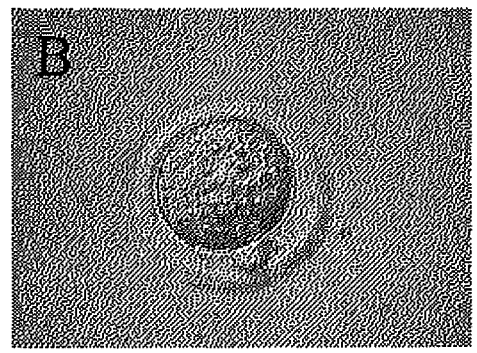
Figure 3:
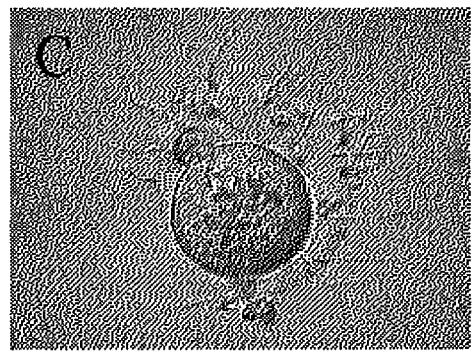
Figure 3:
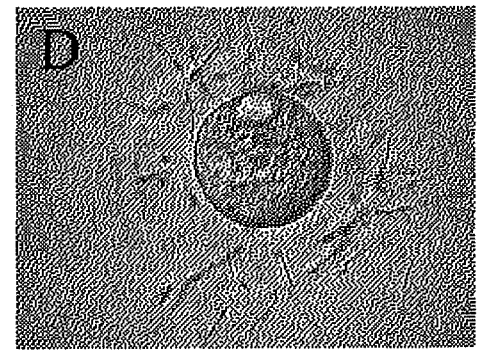

Further, the influence of glutathione on swelling of zona pellucida was confirmed. Fresh unfertilized ovums in which cumulus cells had been removed prepared according to the above-described "1. Preparation of ovum" were treated with HTF culture media containing glutathione at various concentration at 37° C. for 6 hours, then, the area in zona pellucida was photographed under a microscope and measured by an image analysis software. The results are shown in FIG. 2. The conditions of zona pellucida at glutathione concentrations of 0 mM, 1 mM, 2 mM and 10 mM were observed by an invert microscope. The results are shown in FIG. 3.

By these results, swelling of zona pellucida was confirmed depending on the glutathione concentration, and particularly, swelling of zona pellucida was recognized remarkably at concentrations of 2 mM or more.

According to the results of an improvement in fertilization rate and the results of swelling of zona pellucida described above, a remarkable improvement in fertilization rate was confirmed at glutathione concentrations of 1.0 mM or more and less than 1.50 mM (0.30 mg/ml or more and less than 0.46 mg/ml) though swelling of zona pellucida did not appear remarkably.

Example 3

Action of Combination Use of Methyl-β-Cyclodextrin and Glutathione

The influence of glutathione and methyl-β-cyclodextrin (MBCD) in pre-incubation of sperms was confirmed in the same manner as in Example 1. The TYH culture medium used for pre-incubation of sperms was prepared according to the above-described composition excepting that polyvinyl alcohol (1.0 mg/ml, available from SIGMA) was used instead of bovine serum albumin, and methyl-β-cyclodextrin (0.75 mM, available from SIGMA) was added. Further, the concentration of glutathione in the TYH culture medium was 1 mM, preparation was carried out in the same manner as in Example 1, and glutathione was added to the TYH culture medium directly before use. The influence on fertilization rate was compared among those containing methyl-β-cyclodextrin, those containing glutathione and those containing both compounds.

Fertilization was conducted with 90 µl of an HTF culture medium (in the case of addition of glutathione, the concentration was 1 mM) containing cumulus-oocyte complexes (COCs), in the same manner as in Example 1 (IVF/glutathione in table). As the sperm, frozen sperms of C57BL/6J mice were used, and processed according to FIG. 1. Thawed sperms were pre-incubated in a TYH culture medium (±glutathione, ±methyl-β-cyclodextrin) at 37° C. for 30 minutes, and sperms showing motility were collected and used for fertilization. The experiment was conducted five times. The results are shown in Table 7 below.

TABLE 7

| sperm pre-incubation | | IVF | number of dissemninated oocyte | number of 2-cell stage embryo (%) |
|---|---|---|---|---|
| MBCD | glutathione | glutathione | | |
| − | − | − | 337 | 47(14) |
| | | + | 381 | 136(36) |
| − | + | − | 344 | 53(15) |
| | | + | 371 | 140(38) |
| + | − | − | 323 | 210(65) |
| | | + | 328 | 286(87) |
| + | + | − | 364 | 240(66) |
| | | + | 368 | 317(86) |

Also in the above-described results, a remarkable improvement in fertilization rate is shown, by treating unfertilized ovums with glutathione.

In contrast, regarding pre-incubation of sperms, an improvement in fertilization rate was not observed even if sperms were pre-incubated with 1 mM glutathione. However, when sperms were treated with methyl-β-cyclodextrin, fertilization rate was improved, and further, in the case of combination with a treatment of an unfertilized ovum with glutathione, fertilization rate was significantly improved.

Example 4

Elimination of Zona Pellucida of Unfertilized Ovum (1)

Figure 7:
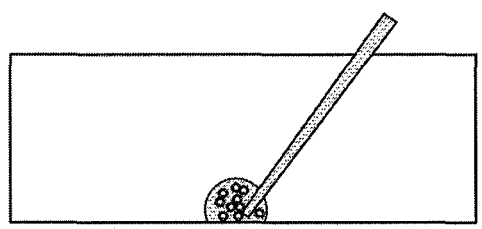
FIG. 7 is a view showing the outline of a method for eliminating the zona pellucida of an unfertilized ovum (embryo), used in the present invention.
Figure 7:
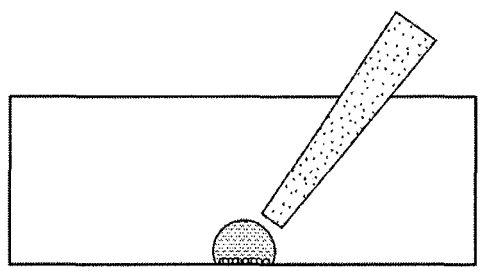
Figure 7:
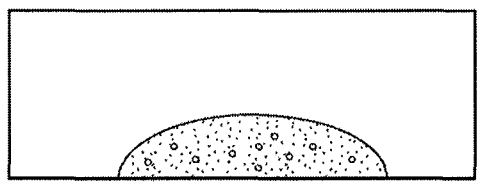

Mouse fresh unfertilized ovums in which cumulus cells had been removed prepared according to the above-described "1. Preparation of ovum" were prepared. The ovums were treated with an HTF culture medium containing glutathione at a concentration of 100 mM (30.7 mg/ml) at 20° C. for 90 seconds. The operation conducted is explained referring to FIG. 7. Onto the bottom of a petri dish, 10 µl of a glutathione-containing HTF culture medium was dropped, and 10 embryos were inserted into this. After 30 seconds, zona pellucida began to become thin (swell), and after 90 seconds, zona pellucida disappeared completely. After confirmation of disappearance of zona pellucida, the embryos were immediately diluted with 1000 µl of an HTF culture medium containing no glutathione, for avoiding damage on the embryos. Thereafter, the zona pellucida-eliminated embryos were transferred into a 100 µl drop of HTF, and further, transferred into a 100 µl drop of HTF twice, thus continuing incubation.

Figure 4:
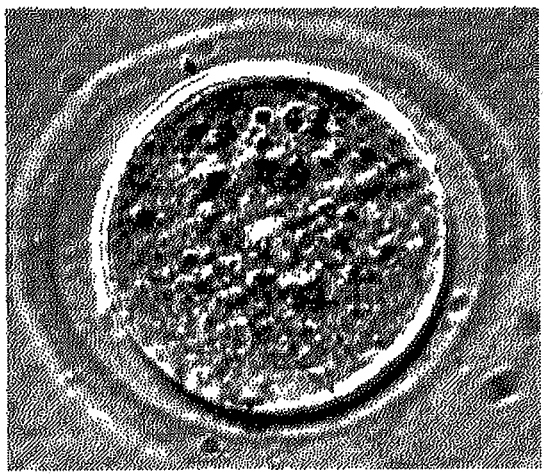
FIG. 4a is a micrograph of a mouse unfertilized ovum not treated with reduced glutathione.
FIG. 4b is a micrograph of a mouse unfertilized ovum treated with reduced glutathione.
FIG. 4c is a micrograph showing division of an ovum after fertilization.
Figure 4:
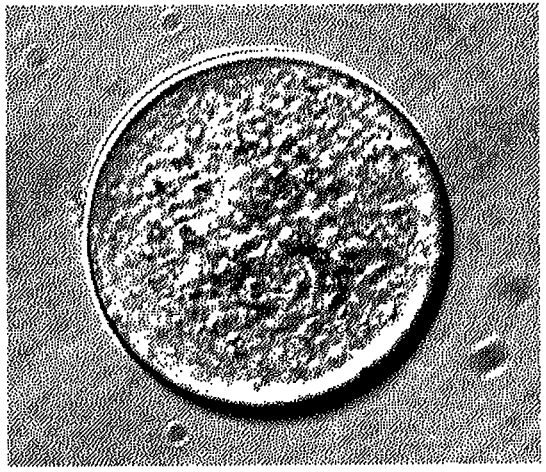
Figure 4:
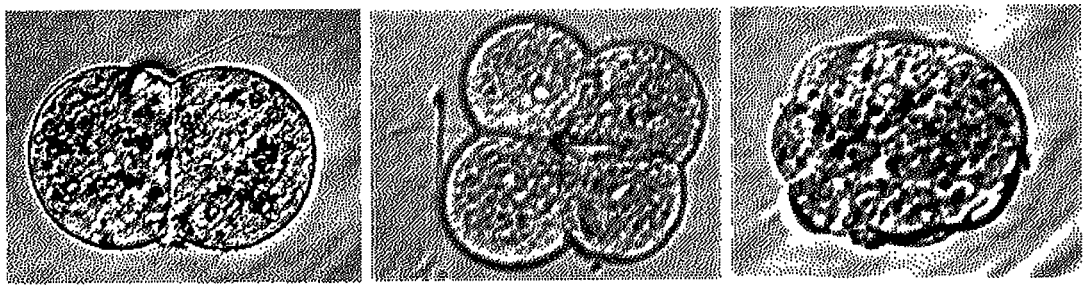

The condition of zona pellucida-elimination was confirmed by an invert microscope. FIG. 4a shows an unfertilized ovum before treating with glutathione. FIG. 4b shows an unfertilized ovum after treating with glutathione. As shown in the figures, the zona pellucida of an unfertilized ovum was eliminated as a result of the glutathione treatment.

Next, frozen sperms of C57BL/6 mice generally showing low fertilizing capacity were used and fertilization was conducted in the same manner as in Example 1 excepting that the zona pellucida-eliminated ovum prepared as described above was used. Even if sperms showing low fertilizing capacity were used, fertilization occurred and the development of an ovum (ovum division) was confirmed. The results are shown in FIG. 4c.

The above-described experiment was repeated 10 times. As a result, it was confirmed that 70 zona pellucida-eliminated embryos could be produced using 70 embryos and 66 embryos developed to the blastocyst stage. As a result of this, it was confirmed that by eliminating the zona pellucida of an embryo, fertilization is attained and development occurs at very high frequency even if sperms showing low fertilizing capacity were used.

Example 5

Elimination of Zona Pellucida of Unfertilized Ovum (2)

Elimination of the zona pellucida of an unfertilized ovum was conducted in the same manner as in Example 4 excepting use of an HTF culture medium having a glutathione concentration of 50 mM (15.4 mg/ml). In the case of use of glutathione at a concentration of 50 mM, zona pellucida was eliminated completely, however, a time of 7 to 8 minutes was necessary until disappearance of zona pellucida. As a result of repetition of the experiment twice, 20 zona pellucida-eliminated embryos could be produced using 20 embryos.

Example 6

Elimination of Zona Pellucida of Frozen Unfertilized Ovum

Figure 5:
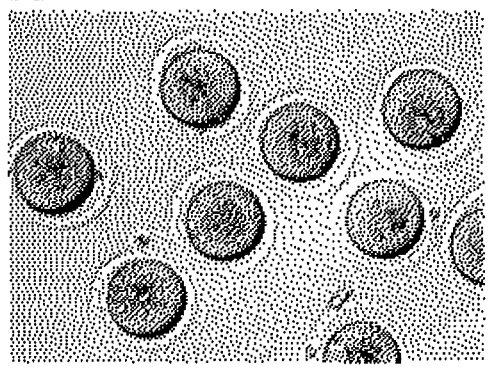
FIG. 5a is a micrograph of a mouse unfertilized ovum (freeze-thawed ovum) not treated with reduced glutathione.
FIG. 5b is a micrograph of a mouse unfertilized ovum (freeze-thawed ovum) treated with reduced glutathione.
FIG. 5c is a micrograph showing the condition of fertilization.
Figure 5:
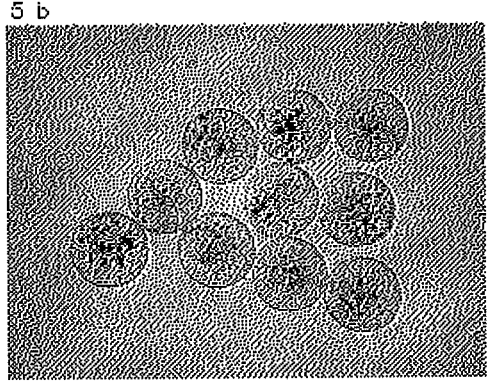
Figure 5:
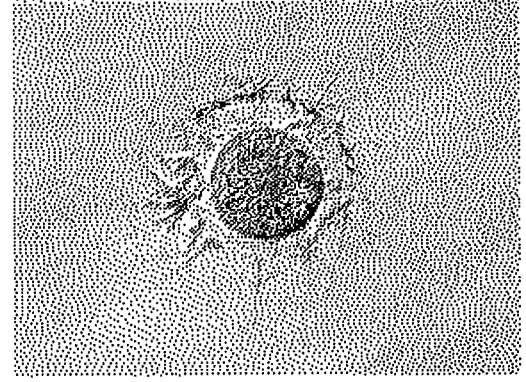

According to an ordinary method, mouse frozen unfertilized ovums were prepared using 8-week old female mice. After thawing of frozen unfertilized ovums, the ovums were treated with an HTF culture medium containing 100 mM glutathione at 20° C. for 90 seconds in the same manner as in Example 4, and the condition was confirmed by a microscope. FIG. 5a shows unfertilized ovums before treating with glutathione. FIG. 5b shows unfertilized ovums after treating with glutathione. As shown in the figures, the zona pellucida of a freeze-thawed unfertilized ovum was eliminated as a result of the glutathione treatment.

As a result of fertilization using unfertilized ovums in which zona pellucida had been eliminated in the same manner as in Example 1, fertilization rate was 25% (125/492). By observation with a microscope, it was shown that intrusion of sperms became easy (FIG. 5c). It was confirmed that the method of the present invention was effective also for a frozen fertilized ovum.

Example 7

Thinning and Elimination of Zona Pellucida and Glutathione Concentration

The influence of the glutathione concentration and the treating time exerted on thinning and elimination of zona pellucida was confirmed. Mouse fresh unfertilized ovums in which cumulus cells had been removed prepared according to the above-described "1. Preparation of oocyte" were prepared, then, 10 µl of an HTF culture medium containing glutathione at various concentrations (5, 10, 25, 50, 100, 200 and 300 mM) was dropped onto the bottom of a petri dish, and 20 ovums were inserted into this, and the time until elimination of zona pellucida was measured. The results are shown in Table 8.

TABLE 8

| gultathione concentration (mM) | condition of zona pellucida | time (second) necessary for lysis of zona pellucida | pH |
|---|---|---|---|
| 5 | thinning | — | 7.3 |
| 10 | thinning | — | 7.4 |
| 25 | thinning | — | 6.1 |
| 50 | elimination | <1,500 | 4.0 |
| 100 | elimination | <60 | 3.5 |
| 200 | elimination | <50 | 3.1 |
| 300 | elimination | <10 | 3.1 |

As is understood from the above-described results, zona pellucida was eliminated at a glutathione concentration of 50 mM or more, and the time necessary for elimination decreased in concentration-dependent manner. With an increase in the glutathione concentration, pH of the treating culture medium also lowers.

Example 9

Rising of Implanting Rate (Offspring Development Rate) by Glutathione Treatment

Fertilization was conducted using mouse frozen sperms of C57BL/6J mice in the same manner as in Example 1. Next, fertilized ovums were washed with an HTF culture medium containing 1 mM glutathione, and further, incubation (development) thereof was conducted. On the next day, fertilization-confirmed embryos (2-cell stage embryo) were collected, and according to the above-described ordinary method, transplanted into female mice and the offspring number was confirmed. The concentration of glutathione in the HTF culture medium was 1 mM, and those fertilized and incubated using an HTF culture medium containing no glutathione were used as the control.

As a result, in the case of fertilization and incubation only with an HTF culture medium, the offspring development rate was 31/80 (38.8%), while in the case of fertilization and incubation with a glutathione-containing HTF culture medium, it was 43/80 (53.8%). It was shown that by thinning of zona pellucida by using glutathione, the offspring development rate (implanting rate) increased, and offsprings could be produced effectively.

Example 10

Figure 6:
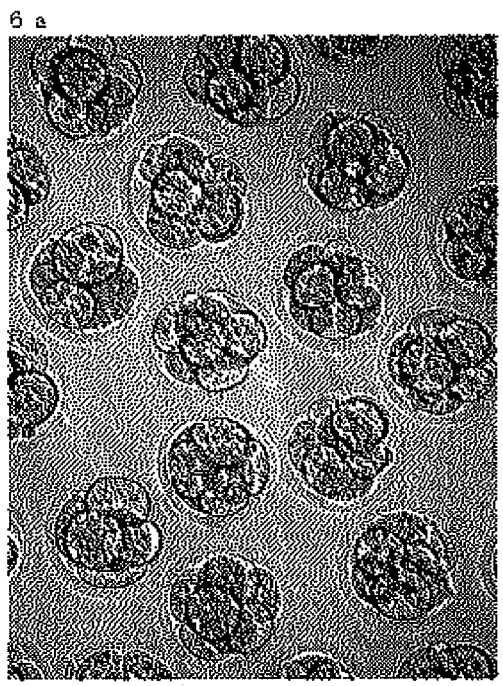
FIG. 6a is a micrograph of a mouse embryo in the early stages of development (8-cell stage embryo) not treated with reduced glutathione.
FIG. 6b is a micrograph of a mouse embryo in the early stages of development (8-cell stage embryo) treated with reduced glutathione.
Figure 6:
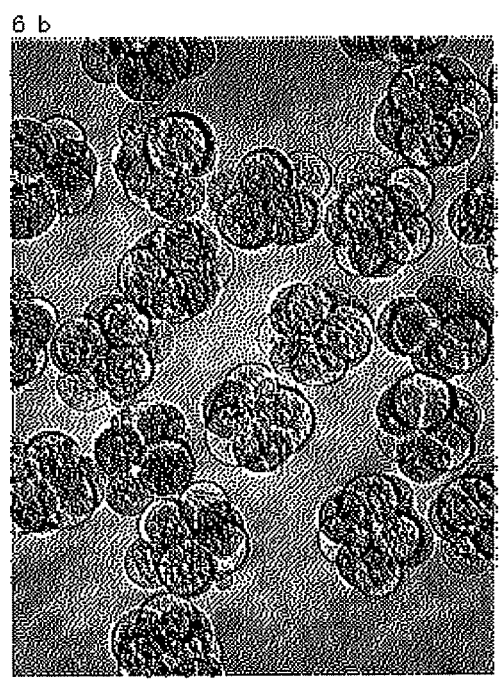

Elimination of Zona Pellucida of Mouse Embryo in the Early Stages of Development The zona pellucida of a mouse embryo in the early stages of development (8-cell stage embryo) used for production of a genetically modified mouse was eliminated. Specifically, the prepared mouse embryo in the early stages of development (8-cell stage embryo) was treated with an HTF culture medium containing glutathione at a concentration of 100 mM at 20° C. for 90 seconds, and the condition thereof was confirmed by a microscope. FIG. 6a shows mouse embryos before treating with glutathione. FIG. 6b shows mouse embryos after treating with glutathione. As shown in the figures, as a result of the glutathione treatment, elimination of zona pellucida from a 8-cell stage embryo used for production of a genetically modified mouse could be conducted easily, and mouse embryos suitable for co-incubation with ES cells were prepared.

Example 11

Confirmation of Thiol in Glutathione-Treated Ovum Zona Pellucida

Figure 8:
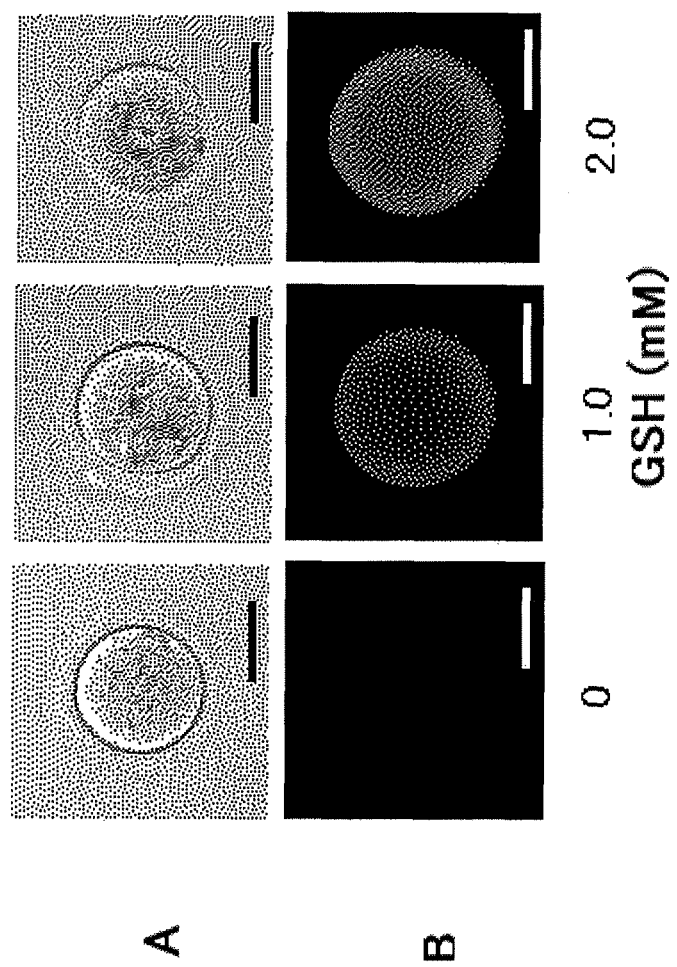
FIG. 8A is a micrograph of a mouse unfertilized ovum treated with reduced glutathione of each concentration.
FIG. 8B is a micrograph of a mouse unfertilized ovum treated with reduced glutathione of each concentration, stained with a thiol-reactive fluorescent dye.
Figure 9:
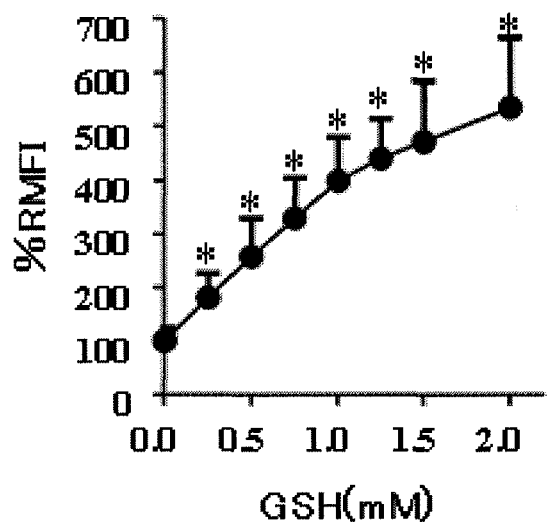
FIG. 9 shows fluorescence intensity, in the case of staining of a mouse unfertilized ovum treated with reduced glutathione of each concentration with a thiol-reactive fluorescent dye. The intensity is expressed in terms of relative intensity, based on 100% in the case of no treatment with reduced glutathione.

Mouse fresh unfertilized ovums in which cumulus cells had been removed prepared according to the above-described "1. Preparation of oocyte" were prepared, then, 100 µl of an HTF culture medium containing glutathione at various concentrations (0, 0.25, 0.5, 0.75, 1.0, 1.25, 1.5 and 2.0 mM) was dropped onto the bottom of a petri dish, and 50 embryos were inserted into this, and treated at 37° C. for 1 hour. Thereafter, a protein thiol in zona pellucida was detected by using a thiol-reactive fluorescent dye (Alexa Fluor 488 C5-maleimide). The results of fluorescent labeling are shown in FIG. 8. The fluorescent intensity of an ovum treated with glutathione of each concentration is shown in FIG. 9 (100% for control).

It was confirmed by this result that the fluorescent intensity in zona pellucida increased depending on the concentration of glutathione used for treatment, namely, the free thiol group in zona pellucida increased. This shows that glutathione acts on a disulfide bond in zona pellucida, to cut at least part of its bond. Further, it is shown that with increasing in bond cut, swelling of zona pellucida progresses more.

Example 12

Thinning of Zona Pellucida with Reducing Agent Other than Glutathione

The influence of other reducing agents (DTT, ascorbic acid (VC) and epicatechin (EC)) exerted on thinning and swelling of zona pellucida was confirmed in the same manner as in Example 2. The extent of swelling of the zona pellucida of an unfertilized ovum by the concentration of each reducing agent was photographed under a microscope, and determined according to the following formula.

% Relative area in ZP=(area of zona pellucida in each experiment/area of zona pellucida at 0 mM)×100

Figure 10:
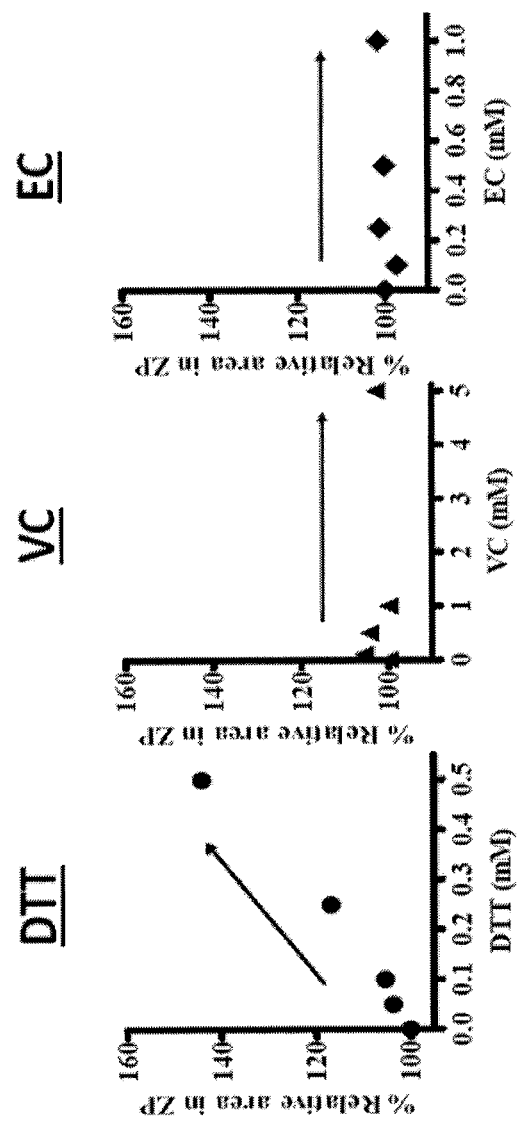
FIG. 10 shows the results of measurement of swelling of zona pellucida, in the case of treatment of a mouse unfertilized ovum with reducing agents having SH groups (DTT, ascorbic acid and epicatechin). In the case of no treatment with each reducing agent, swelling is defined as 100%.

The results are shown in FIG. 10.

Figure 11:
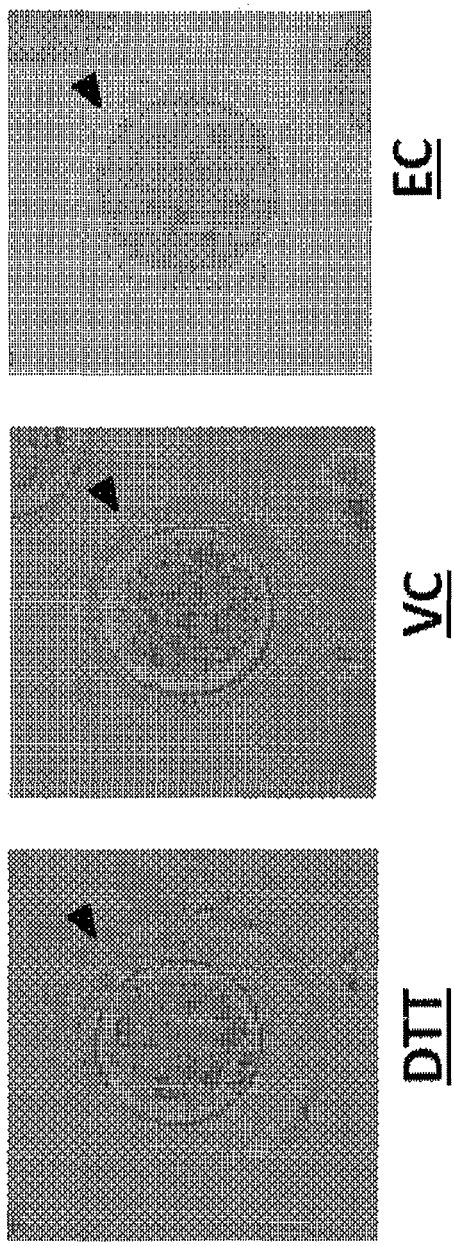
FIG. 11 is a micrograph of a mouse unfertilized ovum treated with reducing agents having SH groups (DTT, ascorbic acid and epicatechin).

The conditions of zona pellucida of unfertilized ovums treated with culture media to which DTT, ascorbic acid and epicatechin had been added at a concentration of 0.5, 5 and 1 mM respectively are shown in FIG. 11.

Based on the results in FIG. 10 and FIG. 11, thinning and swelling of zona pellucida by treatment with DTT were confirmed. In contrast, however, thinning or swelling of zona pellucida did not occur with ascorbic acid or epicatechin as a reducing agent having no SH group.

Example 13

Improvement of Fertilization Rate in Mice of Various Lineages by Glutathione

In the same manner as in Example 1, an improvement of fertilization rate by glutathione was investigated using mice of various lineages. Regarding the sperms, fresh sperms and frozen sperms pre-incubated with MBCD were used in performing fertilization. The concentration of glutathione in an HTF culture medium was 0.25 mM in the case of fresh sperms and 1 mM in the case of frozen sperms. The sperms were pre-incubated with a MBCD-containing TYH culture medium (no glutathione) before fertilization, in the same manner as in Example 3. The pre-incubation time was 1 hour in the case of fresh sperms and 30 minutes in the case of frozen sperms. The results for fresh sperms are shown in Table 9 and the results for frozen sperms are shown in Table 10.

TABLE 9

| 1. In vitro fertilization using fresh sperms | | |
|---|---|---|
| mouse lineage | Glutathione (mM) | fertilization rate (%) |
| BALB/c | 0 | 47.3 |
|  | 0.25 | 74.7 |
| C3H/He | 0 | 70.0 |
|  | 0.25 | 97.5 |
| C57BL/6J | 0 | 87.0 |
|  | 0.25 | 95.6 |
| C57BL/6N | 0 | 85.3 |
|  | 0.25 | 90.9 |
| DBA/2N | 0 | 86.0 |
|  | 0.25 | 95.2 |
| ICR | 0 | 70.0 |
|  | 0.25 | 93.8 |
| BDF1 | 0 | 80.0 |
|  | 0.25 | 94.2 |
| B6C3F1 | 0 | 87.0 |
|  | 0.25 | 97.7 |
| 129T2/SvEmsJ | 0 | 21.5 |
|  | 0.25 | 84.9 |

TABLE 10

2. in vitro fertilization using cryopreserved sperms

| mouse lineage | Glutathione (mM) | fertilization rate (%) |
|---|---|---|
| BALB/c | 0 | 48.0 |
| | 1 | 68.3 |
| C3H/He | 0 | 65.0 |
| | 1 | 98.0 |
| C57BL/6J | 0 | 10.0 |
| | 1 | 97.9 |
| C57BL/6N | 0 | 4.6 |
| | 1 | 90.9 |
| DBA/2N | 0 | 80.0 |
| | 1 | 95.8 |
| ICR | 0 | 60.0 |
| | 1 | 94.9 |
| BDF1 | 0 | 70.0 |
| | 1 | 98.3 |
| B6C3F1 | 0 | 59.0 |
| | 1 | 87.6 |
| 129T2/SvEmsJ | 0 | 22.4 |
| | 1 | 82.1 |

In the case of fresh sperms, a sufficient improvement in fertilization rate was observed at a glutathione concentration of 0.25 mM. Further, a remarkable improvement in fertilization rate for frozen sperms by glutathione addition was confirmed in all mouse lineages.

Example 14

Improvement in Fertilization Rate for Refrigerated Sperms by MBCD and Glutathione In the same manner as in Example 1, an improvement in fertilization rate by MBCD and glutathione was investigated using refrigerated sperms of C57BL/6J mice. The sperms were pre-incubated with a MBCD-containing TYH culture medium (no glutathione) before fertilization, in the same manner as in Example 3. The pre-incubation time was 1 hour. As a result, the fertilization rate in the case of no addition of glutathione was 52.4%, while the fertilization rate in the case of addition of glutathione at a concentration of 0.5 mM increased to 85.4%.

The above-described detailed descriptions simply explain the object and the subject matter of the present invention, and do not limit the scope of the appended claims. Without deviating from the scope of the appended claims, various alterations and substitutions for embodiments described are apparent for those skilled in the art based on teachings described in the present specification.

INDUSTRIAL APPLICABILITY

The present invention is useful for in vitro fertilization of a mammal and transplantation into uterus (implantation) of a fertilized ovum. Further, the present invention is a useful technology which can be used in a step of producing a genetically modified animal.

The invention claimed is:

1. A fertilizing method comprising:
   (a) pre-incubating mammal sperm with a sperm pre-incubation culture medium containing 0.1 mM or more and 20 mM or less cyclodextrin and 0.1 mM or more and 10 mM or less calcium,
   (b) adding an unfertilized mammal ovum into a medium containing reduced glutathione at a concentration of 50 mM or more and 300 mM or less in terms of SH equivalent, and preparing an unfertilized ovum treated with the reduced glutathione, for thinning or elimination of the zona pellucida of the unfertilized ovum, and
   (c) adding the sperm pre-incubated in step (a) into a fertilization culture medium containing the unfertilized ovum treated with the reduced glutathione in step (b) and performing insemination.

2. The fertilizing method according to claim 1, wherein the unfertilized ovum is a mouse unfertilized ovum.

3. The fertilizing method according to claim 1, wherein the cyclodextrin is methyl-β-cyclodextrin.

4. The fertilizing method according to claim 2, wherein the sperm to be used for fertilization are mouse frozen sperm and the pre-incubation in step (a) is conducted for at least 10 min.

5. The fertilizing method according to claim 1, wherein the fertilization culture medium in step (c) contains substantially no reduced glutathione.

6. The fertilizing method according to claim 1, wherein the sperm used for fertilization are fresh sperm, frozen sperm, refrigerated sperm or a combination thereof, and wherein the sperm pre-incubation culture medium in step (a) contains no reduced glutathione.

* * * * *